United States Patent
Pan et al.

(10) Patent No.: US 11,702,413 B2
(45) Date of Patent: Jul. 18, 2023

(54) ORGANIC SEMICONDUCTING COMONOMER

(71) Applicant: PHILLIPS 66 COMPANY, Houston, TX (US)

(72) Inventors: Hualong Pan, Bartlesville, OK (US); Kathy Woody, Bartlesville, OK (US); Brian J. Worfolk, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 17/002,805

(22) Filed: Aug. 26, 2020

(65) Prior Publication Data
US 2021/0061797 A1    Mar. 4, 2021

Related U.S. Application Data

(60) Provisional application No. 62/892,359, filed on Aug. 27, 2019.

(51) Int. Cl.
*C07D 417/14* (2006.01)

(52) U.S. Cl.
CPC ................. *C07D 417/14* (2013.01)

(58) Field of Classification Search
CPC .................................. C07D 417/14
USPC ........................................ 548/126
See application file for complete search history.

(56) References Cited

U.S. PATENT DOCUMENTS

2014/0124035 A1    5/2014  Byrne et al.

FOREIGN PATENT DOCUMENTS

WO    WO-2019091995 A1 *  5/2019 ........... C08G 61/126

* cited by examiner

*Primary Examiner* — Kahsay Habte
(74) *Attorney, Agent, or Firm* — Phillips 66 Company

(57) ABSTRACT

A comonomer comprising:

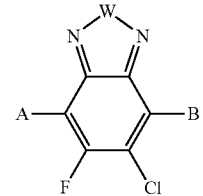

wherein W is selected from the group consisting of: S, Se, O, and N-Q; and Q is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring. In this comonomer, A and B are independently selected from the group consisting of: H, Br, an aryl group, and a heteroaryl group.

5 Claims, 22 Drawing Sheets

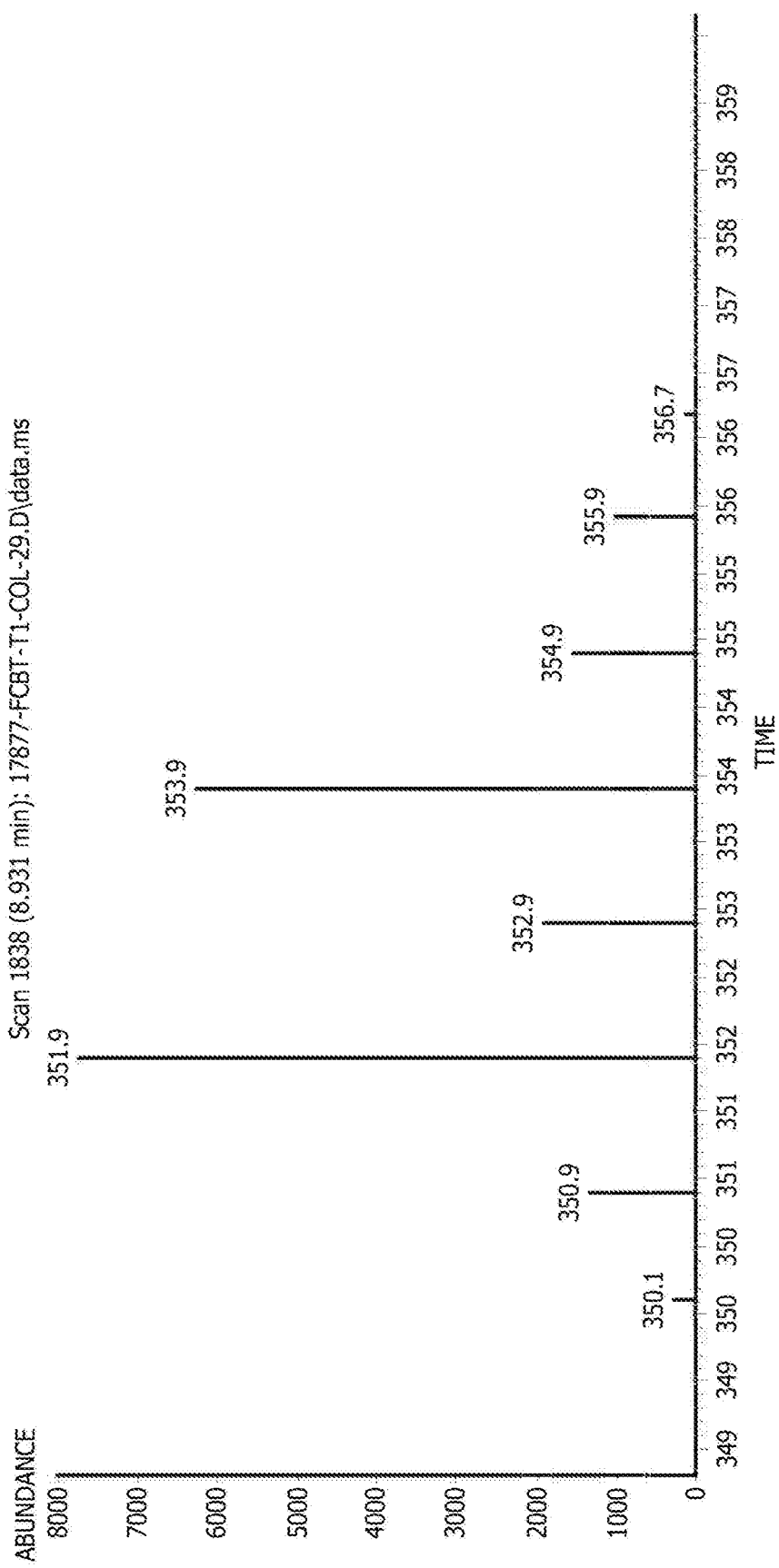

ORGANIC SEMICONDUCTING COMONOMER

CROSS-REFERENCE TO RELATED APPLICATIONS

This application is a non-provisional application which claims the benefit of and priority to U.S. Provisional Application Ser. No. 62/892,359 filed Aug. 27, 2019, titled "Organic Semiconducting Comonomer," which is hereby incorporated by reference in its entirety.

STATEMENT REGARDING FEDERALLY SPONSORED RESEARCH OR DEVELOPMENT

None.

FIELD OF THE INVENTION

This invention relates methods of synthesis of organic semiconducting polymers.

BACKGROUND OF THE INVENTION

Solar energy using photovoltaics requires active semiconducting materials to convert light into electricity. Currently, solar cells based on silicon are the dominating technology due to their high power conversion efficiency. Recently, solar cells based on organic materials showed interesting features, especially on the potential of low cost in materials and processing.

Organic photovoltaic cells have many potential advantages when compared to traditional silicon-based devices. Organic photovoltaic cells are light weight, economical in the materials used, and can be deposited on low cost substrates, such as flexible plastic foils. However, organic photovoltaic devices typically have relatively low power conversion efficiency (the ratio of incident photons to energy generated).

There exists a need for a polymer to create organic photovoltaic cells that has high power conversion efficiency while maintaining open-circuitry voltage short-circuit current density, and fill factor.

BRIEF SUMMARY OF THE DISCLOSURE

A comonomer comprising:

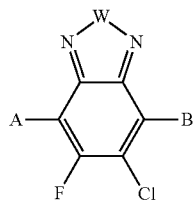

wherein W is selected from the group consisting of: S, Se, O, and N-Q; and Q is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring. In this comonomer, A and B are independently selected from the group consisting of: H, Br, an aryl group, and a heteroaryl group.

In an alternate embodiment, the disclosure describes a comonomer comprising:

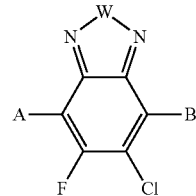

In this embodiment W is S and A and B are independently selected from the group consisting of a H, Br, an aryl group, an aryl group connected to a Br, a heteroaryl group, and a heteroaryl group connected to a Br.

In yet another embodiment, the disclosure describes a comonomer comprising

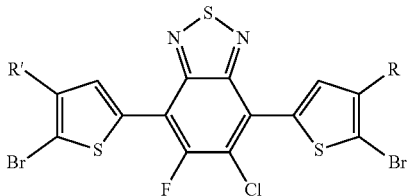

where R and R' are independently selected from H, F, Cl, I, Br, CN, —NCO, —NCS, —OCN, —SCN, —OX, —SX, —NH2, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, a straight-chain or branched carbyl, silyl, or hydrocarbyl, a branched or cyclic alkyl with 1 to 30 atoms, a fused substituted aromatic ring, and a fused unsubstituted aromatic ring.

BRIEF DESCRIPTION OF THE DRAWINGS

A more complete understanding of the present invention and benefits thereof may be acquired by referring to the follow description taken in conjunction with the accompanying drawings in which:

FIG. 16b depicts the spectra of 5-chloro-6-fluoro-4,7-di(thiophen-2-yl)benzo[c][1,2,5]thiadiazole 3'.

DETAILED DESCRIPTION

Figure 1:
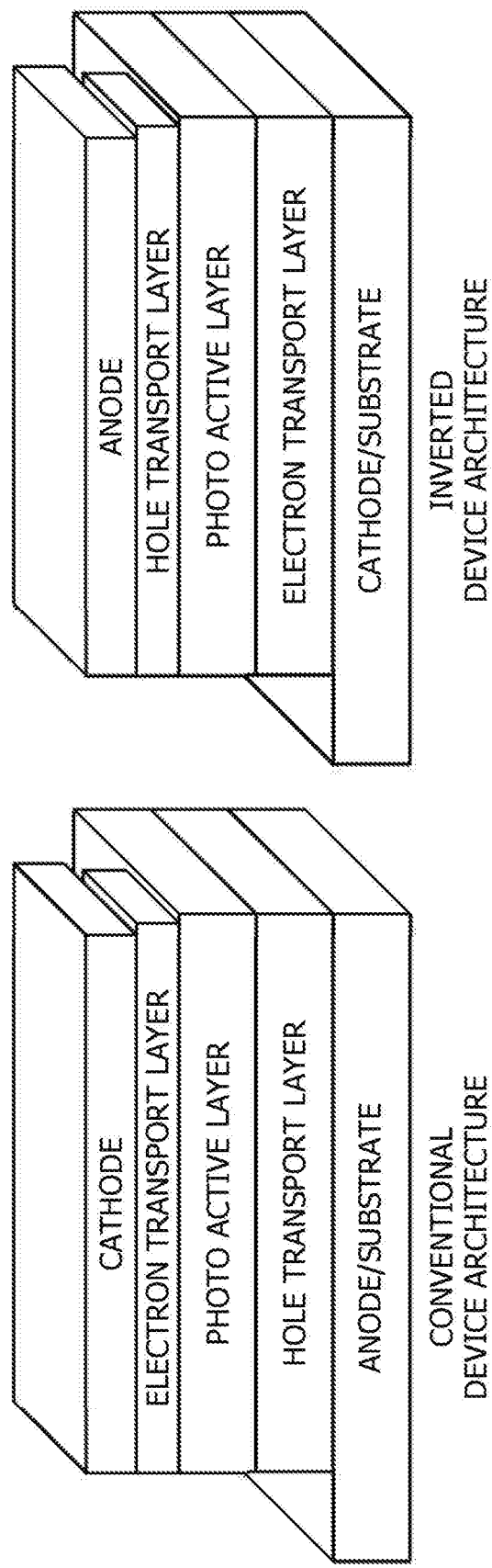
FIG. 1 depicts a conventional device architecture and an inverted device architecture.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

"Alkyl," as used herein, refers to an aliphatic hydrocarbon chains. In one embodiment the aliphatic hydrocarbon chains are of 1 to about 100 carbon atoms, preferably 1 to 30 carbon atoms, more preferably, 1 to 20 carbon atoms, and even more preferably, and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. In this application alkyl groups can include the possibility of substituted and unsubstituted alkyl groups.

"Alkylthiol," as used herein, refers to alkyl groups with a sulfanyl group (—SH) attached.

"Alkoxy," as used herein, refers to the group R—O— where R is an alkyl group of 1 to 100 carbon atoms. In this application alkoxy groups can include the possibility of substituted and unsubstituted alkoxy groups.

"Aryl" as used herein, refers to an optionally substituted, mono-, di-, tri-, or other multicyclic aromatic ring systems or heteroaryl systems having from about 5 to about 50 carbon atoms (and all combinations and subcombinations of ranges and specific numbers of carbon atoms therein), with from about 6 to about 20 carbons being preferred. Non-limiting examples include, for example, phenyl, naphthyl, anthracenyl, and phenanthrenyl. Aryl groups can be optionally substituted with one or with one or more Rx. In this application aryl groups can include the possibility of substituted aryl groups, bridged aryl groups, fused aryl, and heteroaryl groups.

"Heteroaryl" as used herein, reference to a heterocyclyl group derived from a heteroarene by removal of a hydrogen atom from any ring atom. Non-limiting substitutions of the ring atom can be S, O, Te, Se, N, P, Si, Ge, B, and As.

"Ester", as used herein, represents a group of formula —COOR wherein R represents an "alkyl", "aryl", a "heterocycloalkyl" or "heteroaryl" moiety, or the same substituted as defined above.

"Ketone" as used herein, represents an organic compound having a carbonyl group linked to a carbon atom such as —C(O)Rx wherein Rx can be alkyl, aryl, cycloalkyl, cycloalkenyl or heterocycle.

"Amide" as used herein, represents a group of formula "—C(O)NR$^x$R$^y$," wherein R$^x$ and R$^y$ can be the same or independently H, alkyl, aryl, cycloalkyl, cycloalkenyl or heterocycle.

The following examples of certain embodiments of the invention are given. Each example is provided by way of explanation of the invention, one of many embodiments of the invention, and the following examples should not be read to limit, or define, the scope of the invention.

Device Architecture

When used as a photovoltaic device the architecture may be a conventional architecture device, while in others it may be an inverted architecture device. A conventional architecture device typically comprised of multilayered structure with a transparent anode as a substrate to collect positive charge (holes) and a cathode to collect negative charge (electrons), and a photo-active layer sandwiched in between two electrodes. An additional charge transport interlayer is inserted in between active layer and electrode for facile hole and electron transport. Each charge transport layer can be consisted of one or more layers. An inverted device has the same multilayered structure as the conventional architecture device whereas it uses a transparent cathode as a substrate to collect electrons and an anode to collect holes. The inverted device also has the photo-active layer and additional charge transport layers sandwiched in between two electrodes. FIG. 1 depicts a conventional device architecture and an inverted device architecture.

Constitutional Units to Form Monomers

A variety of constitutional units, or comonomers, that can be used to create the monomers for the organic semiconducting polymers. On example of a constitutional unit can be unit A

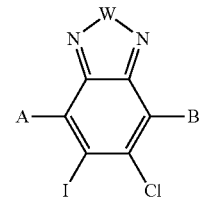

which can be used to form the following comonomer

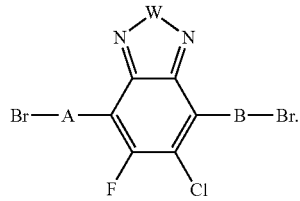

In this embodiment: W could be S, Se, O, or N-Q; Q a straight-chain or branched carbyl, silyl, or hydrocarbyl, a branched or cyclic alkyl with 1 to 30 atoms, a fused substituted aromatic ring, and a fused unsubstituted aromatic ring. The fused substituted aromatic rings can fused with H, Cl, F, CN, a straight-chain or branched carbyl, silyl, or hydrocarbyl, a branched or cyclic alkyl with 1 to 30 atoms, and an aromatic ring.

In an alternative embodiment, when W is N-Q; Q can be independently selected from, H, F, Cl, I, S, Br, CN, —NCO, —NCS, —OCN, —SCN, —OX, —SX, —NH2, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups; and A and B are H.

In one embodiment, A and B are identical. In another embodiment, A and B are not identical. In yet another embodiment A and B are independently selected from a Br, an aryl group, or heteroaryl group. a monoaromatic group, a bi-aromatic group, a tricyclic aromatic group, or a heteroaromatic group. Alternate embodiments of A and B can also include:

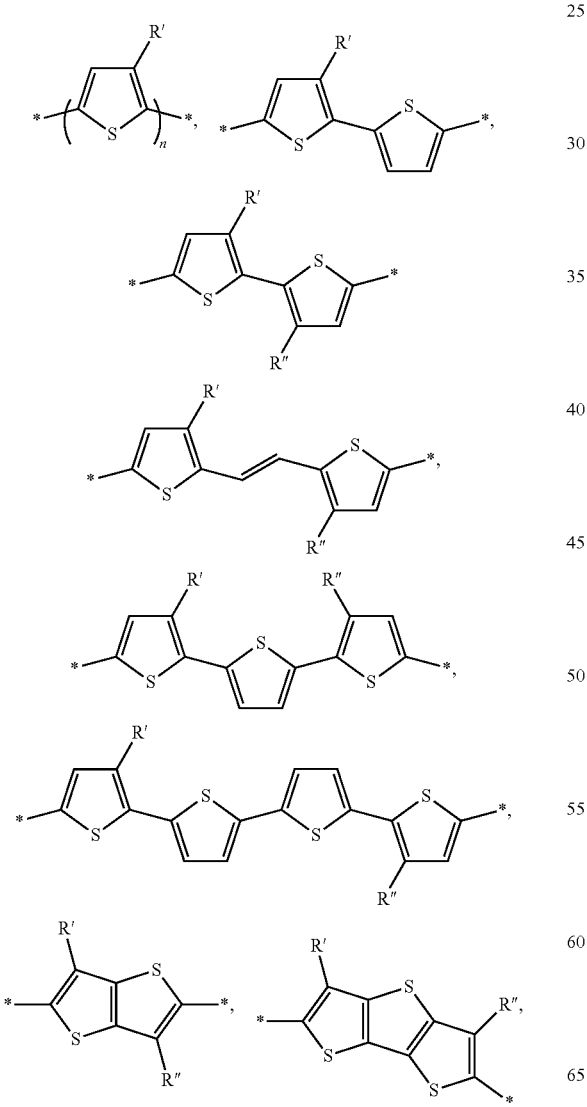

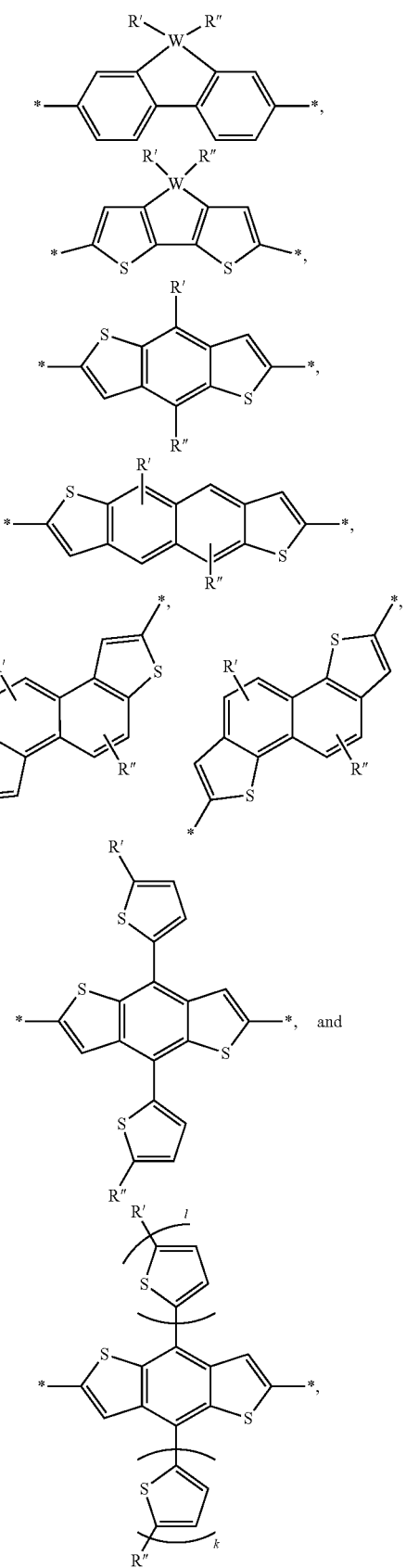

wherein W is selected from the group consisting of: C, Si and Se; R' and R" can be independently selected from the group consisting of: H, Cl, F, CN, an alkyl group, an alkoxy group, an aryl group, a $C_{6-20}$ alkyl group, a —O—$C_{6-20}$ alkyl group, a —O—$C_{6-20}$ alkenyl group, a —O—$C_{6-20}$ haloalkyl group, a —S—$C_{6-20}$ alkyl group, a —S—$C_{6-20}$ alkenyl group, a —S—$C_{6-20}$ haloalkyl group, a -thienyl-$C_{6-20}$ alkyl group, a -thienyl-$C_{6-20}$ alkenyl group, and a -thienyl-$C_{6-20}$ haloalkyl group.

Alternate examples of constitutional units include:

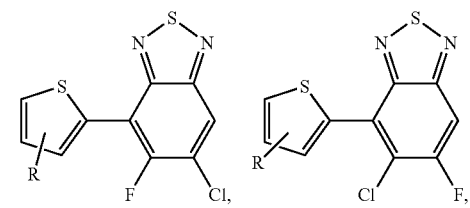

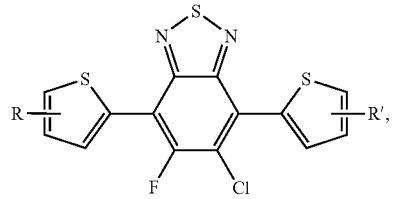

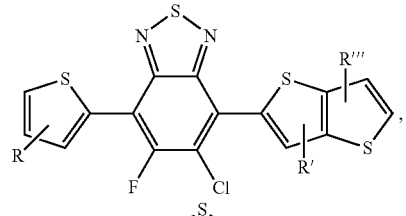

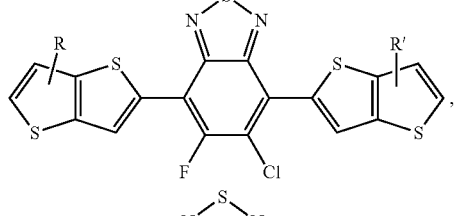

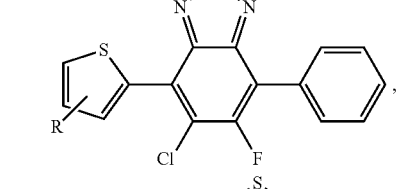

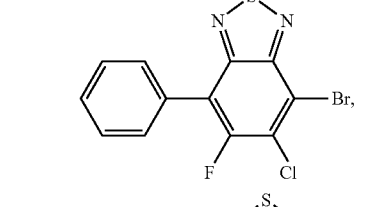

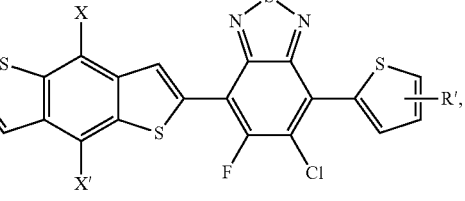

-continued

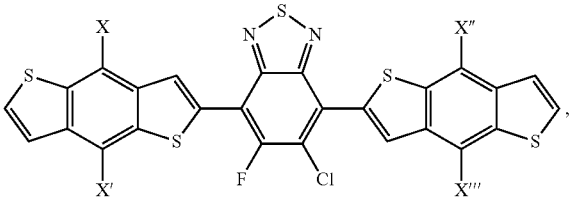

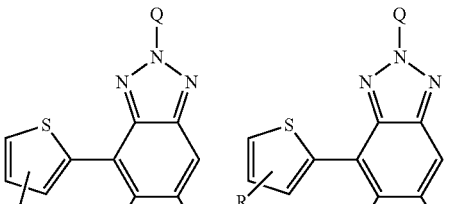

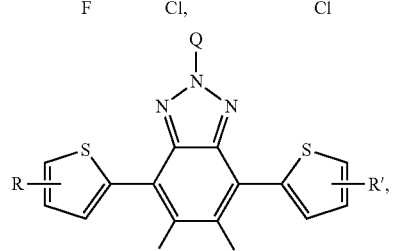

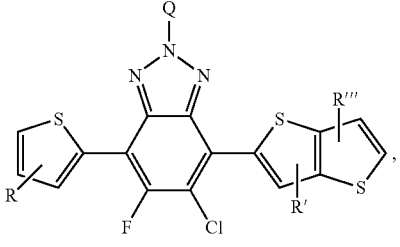

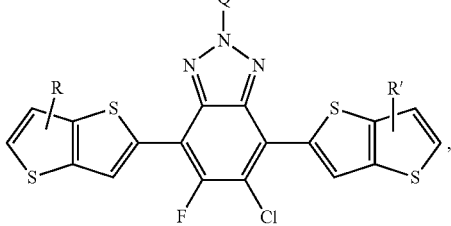

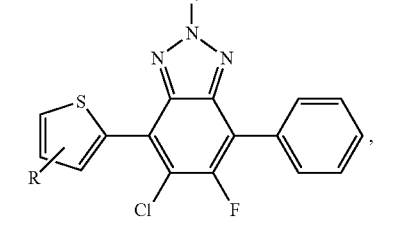

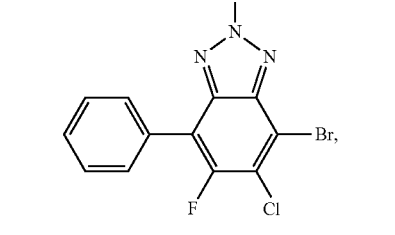

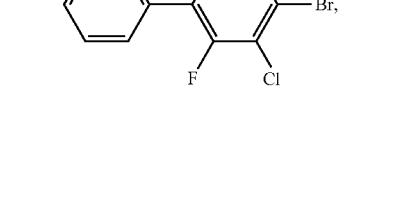

-continued

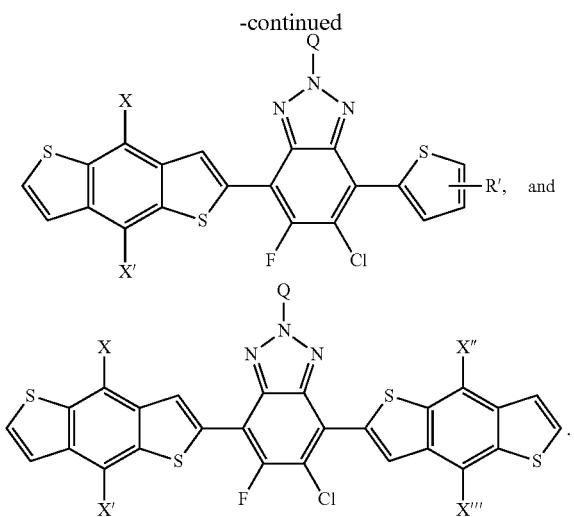

In this embodiment: W could be S, Se, O, or N-Q; Q a straight-chain or branched carbyl, silyl, or hydrocarbyl, a branched or cyclic alkyl with 1 to 30 atoms, a fused substituted aromatic ring, and a fused unsubstituted aromatic ring. The fused substituted aromatic rings can fused with H, Cl, F, CN, a straight-chain or branched carbyl, silyl, or hydrocarbyl, a branched or cyclic alkyl with 1 to 30 atoms, and an aromatic ring.

R', R", X, X', X", X''' can be independently selected from the group consisting of: H, Cl, F, CN, an alkyl group, an alkoxy group, an aryl group, a $C_{6-20}$ alkyl group, a —O—$C_{6-20}$ alkyl group, a —O—$C_{6-20}$ alkenyl group, a —O—$C_{6-20}$ haloalkyl group, a —S—$C_{6-20}$ alkyl group, a —S—$C_{6-20}$ alkenyl group, a —S—$C_{6-20}$ haloalkyl group, a -thienyl-$C_{6-20}$ alkyl group, a -thienyl-$C_{6-20}$ alkenyl group, and a -thienyl-$C_{6-20}$ haloalkyl group.

Alternative constitutional units or comonomers can also include units B

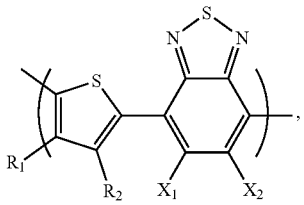

unit C

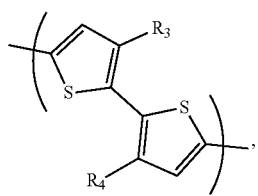

or unit D aryl groups. In this embodiment, R1, R2, R3, and R4 are side chains independently selected from the group consisting of: H, Cl, F, CN, alkyl, alkoxy, alkylthio, ester, ketone and aryl groups. X1 and X2 are independently selected from the group consisting of: H, Cl, F, CN, alkyl, alkoxy, ester, ketone, amide and aryl groups.

The aryl groups of D can be selected from groups such as a benzodithiophenyl group, a silylene-bithiophenyl group, a carbazolyl group, and a dibenzosilole group, each of which can be optionally substituted as described herein. For example, the benzodithiophenyl group, the silylene-bithiophenyl group, the carbazolyl group, and the dibenzosilole group can be substituted with one, two, three or four solubilizing groups. Each solubilizing group can be a linear or branched aliphatic group (e.g., an alkyl group, an alkenyl group, an alkoxy group, or an alkylthio group) having 6-20 carbon atoms. In particular embodiments, each solubilizing group can be a branched C6-20 alkyl group or a branch C6-20 alkoxy group. Other examples of aryl groups such as polycyclic hetroaryl groups of D can include:

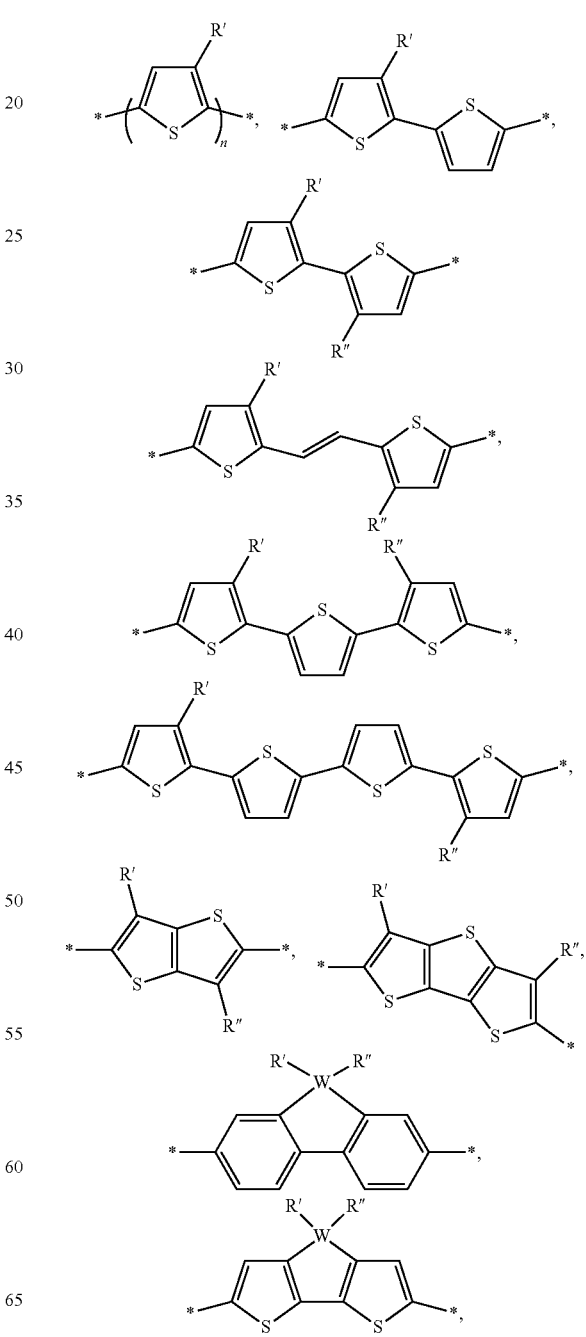

-continued

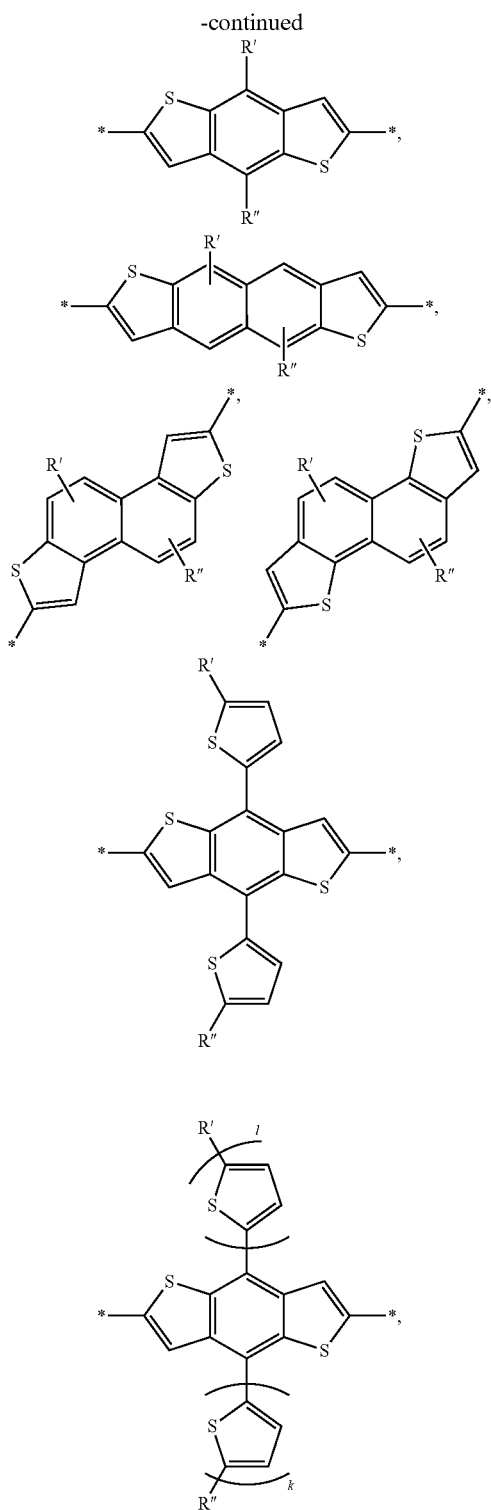

In the above examples W can be C, Si or Se. R', R" can be independently selected from H, Cl, F, CN, an alkyl group, an alkoxy group, an aryl group, a $C_{6-20}$ alkyl group, a —O—$C_{6-20}$ alkyl group, a —O—$C_{6-20}$ alkenyl group, a —O—$C_{6-20}$ haloalkyl group, a —S—$C_{6-20}$ alkyl group, a —S—$C_6$-20 alkenyl group, a —S—$C_{6-20}$ haloalkyl group, a -thienyl-$C_{6-20}$ alkyl group, a -thienyl-$C_{6-20}$ alkenyl group, and a -thienyl-$C_{6-20}$ haloalkyl group In another embodiment, unit E can be

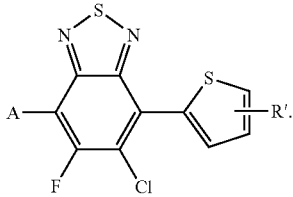

In this embodiment, A can be any aryl and heteroaryl group, preferably a mono-, bi- or tricyclic aromatic or heteroaromatic group with up to 40 C atoms that may also comprise condensed rings and is optionally substituted with one or more groups R, and wherein one or more carbon atoms are optionally substituted by a heteroatom, which is preferably selected from N, P, As, O, S, Se and Te. R' can be selected from: H, F, Cl, I, Br, CN, —NCO, —NCS, —OCN, —SCN, —OX, —SX, —NH₂, —C(=O)X, —C(=O)—OX, —OX, —NHX, —NXX', —C(=O)NHX, —C(=O)NXX', —SO₃X, —SO₂X, —OH, —NO₂, CF₃, —SF₅, or straight-chain carbyl, silyl or hydrocarbyl, branched, cyclic alkyl with 1 to 30 atoms, fused aromatic rings, which can be optionally substituted with one or more X or X' groups.

In another embodiment, unit F can be

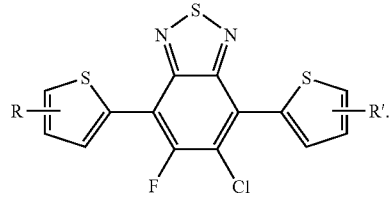

In this embodiment, R and R' can be the same or different and independently selected from selected from: H, F, Cl, I, Br, CN, —NCO, —NCS, —OCN, —SCN, —OX, —SX, —NH₂, —C(=O)X, —C(=O)—OX, —OX, —NHX, —NXX', —C(=O)NHX, —C(=O)NXX', —SO₃X, —SO₂X, —OH, —NO₂, CF₃, —SF, or straight-chain carbyl, silyl or hydrocarbyl, branched, cyclic alkyl with 1 to 30 atoms, fused aromatic rings, which can be optionally substituted with one or more X or X' groups.

In another embodiment, unit G can be

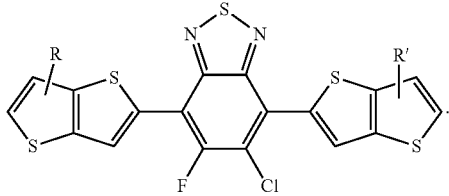

In this embodiment, R and R' can be the same or different and independently selected from, H, F, Cl, I, Br, CN, —NCO, —NCS, —OCN, —SCN, —OX, —SX, —NH₂, —C(=O)X, —C(=O)—OX, —OX, —NHX, —NXX', —C(=O)NHX, —C(=O)NXX', —SO₃X, —SO₂X, —OH, —NO₂, CF₃, —SF₅, or straight-chain carbyl, silyl or hydrocarbyl, branched, cyclic alkyl with 1 to 30 atoms, fused aromatic rings, which can be optionally substituted with one or more X or X' groups.

In another embodiment, unit H can be

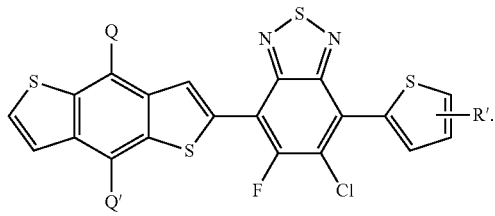

In this embodiment, Q and Q' can be the same or different and independently selected from be straight-chain carbyl, silyl or hydrocarbyl, branched, cyclic alkyl with 1 to 30 atoms, fused aromatic rings, which can be optionally substituted with one or more X or X' groups. R' can be same or different, H, F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups.

In another embodiment, unit I can be

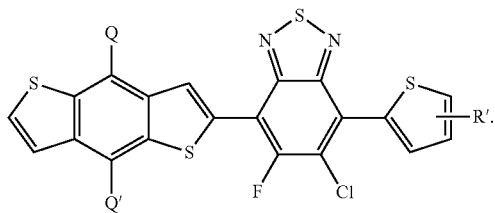

In this embodiment, Q and Q' can be the same or different and independently selected from be straight-chain carbyl, silyl or hydrocarbyl, branched, cyclic alkyl with 1 to 30 atoms, fused aromatic rings, which can be optionally substituted with one or more X or X' groups. R' can be, H, F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups.

In another embodiment, unit J can be

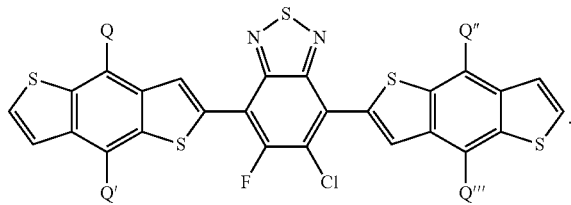

In this embodiment, Q, Q', Q'', and Q''' can be the same or different and independently selected from straight-chain carbyl, silyl or hydrocarbyl, branched, cyclic alkyl with 1 to 30 atoms, fused aromatic rings, which can be optionally substituted with one or more X or X' groups. R and R' can be same or different, H, F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups.

In some other embodiments, the unit can contain one or more of the following monomer repeat units: a benzodithiophene moiety, a cyclopenta dithiazole moiety, a benzothiadiazole moiety, a thiadiazoloquinoxaline moiety, a benzoisothiazole moiety, a benzothiazole moiety, a dithienopyrrole moiety, a dibenzosilole moiety, a thienothiophene moiety, a carbazole moiety, a dithienothiophene moiety, a tetrahydroisoindole moiety, a fluorene moiety, a silole moiety, a cyclopentadithiophene moiety, a thiazole moiety, a selenophene moiety, a thiazolothiazole moiety, a naphthothiadiazole moiety, a thienopyrazine moiety, a silacyclopentadithiophene moiety, a thiophene moiety, an oxazole moiety, an imidazole moiety, a pyrimidine moiety, a benzoxazole moiety, a benzimidazole moiety, a quinoxaline moiety, a pyridopyrazine moiety, a pyrazinopyridazine moiety, a pyrazino quinoxaline moiety, a thiadiazolopyridine moiety, a thiadiazolopyridazine moiety, a benzooxadiazole moiety, an oxadiazolopyridine moiety, an oxadiazolopyridazine moiety, a benzoselenadiazole moiety, a benzobisoxazole moiety, a thienothiadiazole moiety, a thienopyrroledione moiety, or a tetrazine moiety.

For example, the electron donor or acceptor material can include one or more of the following monomer repeat units: a benzodithiophene moiety of formula (1), a benzodithiophene moiety of formula (2), a cyclopentadithiazole moiety of formula (3), a benzothiadiazole moiety of formula (4), a thiadiazoloquinoxaline moiety of formula (5), a benzoisothiazole moiety of formula (6), a benzothiazole moiety of formula (7), a dithienopyrrole moiety of formula (8), a dibenzosilole moiety of formula (9), a thienothiophene moiety of formula (10), a thienothiophene moiety of formula (11), a carbazole moiety of formula (12), a dithienothiophene moiety of formula (13), a tetrahydroisoindole moiety of formula (14), a fluorene moiety of formula (15), a silole moiety of formula (16), a cyclopentadithiophene moiety of formula (17), a thiazole moiety of formula (18), a selenophene moiety of formula (19), a thiazolothiazole moiety of formula (20), a naphthothiadiazole moiety of formula (21), a thienopyrazine moiety of formula (22), a silacyclopentadithiophene moiety of formula (23), a thiophene moiety of formula (24), an oxazole moiety of formula (25), an imidazole moiety of formula (26), a pyrimidine moiety of formula (27), a benzoxazole moiety of formula (28), a benzimidazole moiety of formula (29), a quinoxaline moiety of formula (30), a pyridopyrazine moiety of formula (31), a pyrazinopyridazine moiety of formula (32), a pyrazinoquinoxaline moiety of formula (33), a thiadiazolopyridine moiety of formula (34), a thiadiazolopyridazine moiety of formula (35), a benzooxadiazole moiety of formula (36), an oxadiazolopyridine moiety of formula (37), an oxadiazolopyridazine moiety of formula (38), a benzoselenadiazole moiety of formula (39), a benzobisoxazole moiety of formula (40), a benzobisoxazole moiety of formula (41), a thienothiadiazole moiety of formula (42), a thienopyrroledione moiety of formula (43), or a tetrazine moiety of formula (44):

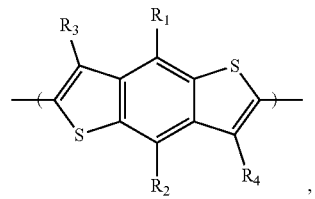(1)
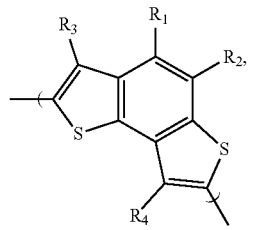(2)
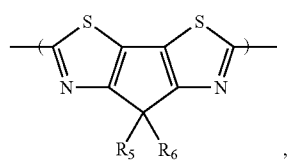(3)
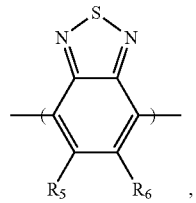(4)
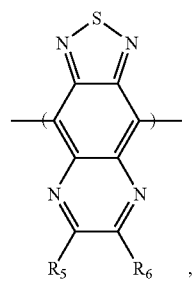(5)
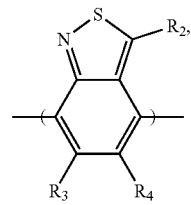(6)
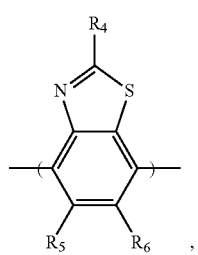(7)
-continued
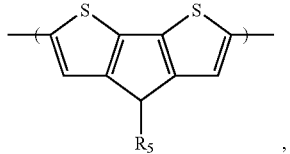(8)
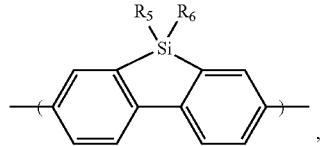(9)
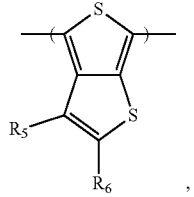(10)
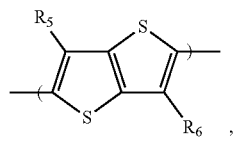(11)
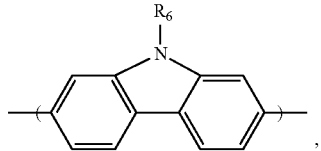(12)
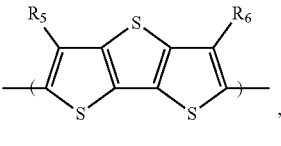(13)
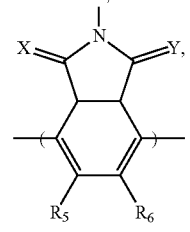(14)
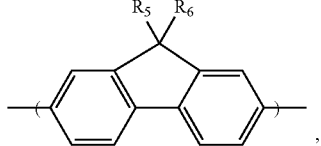(15)
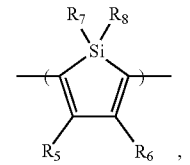(16)

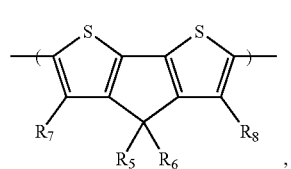 (17)
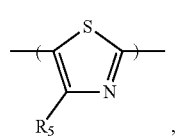 (18)
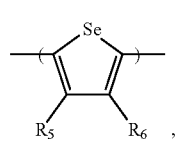 (19)
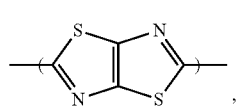 (20)
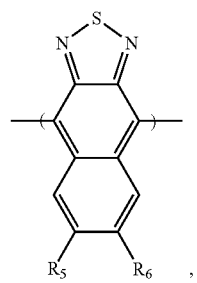 (21)
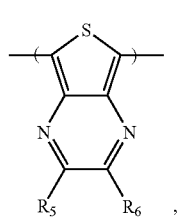 (22)
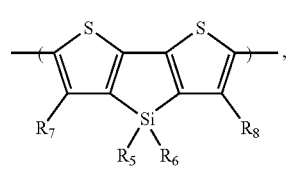 (23)
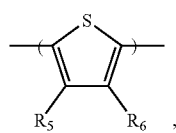 (24)
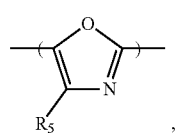 (25)
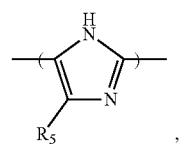 (26)
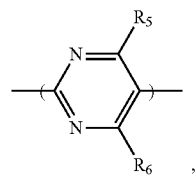 (27)
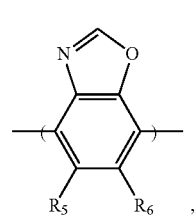 (28)
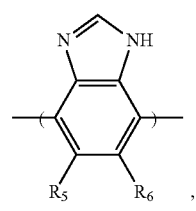 (29)
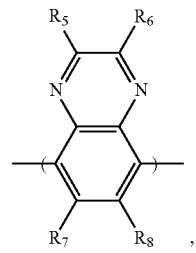 (30)
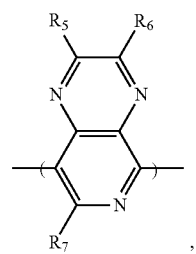 (31)
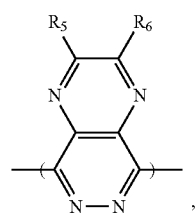 (32)

(33) 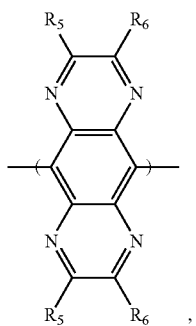

(34) 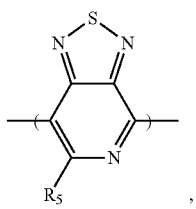

(35) 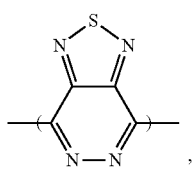

(36) 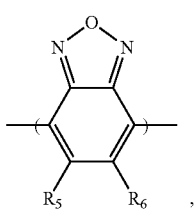

(37) 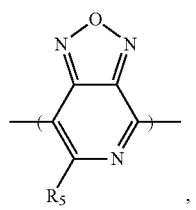

(38) 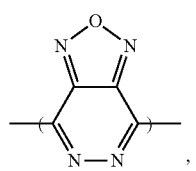

(39) 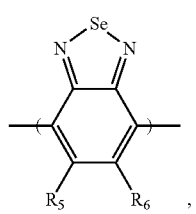

(40) 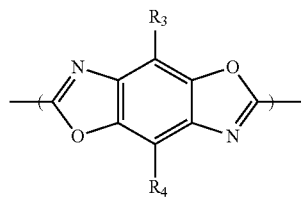

(41) 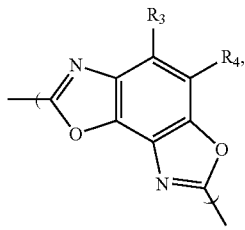

(42) 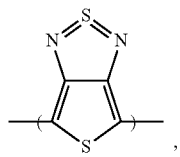

(43) 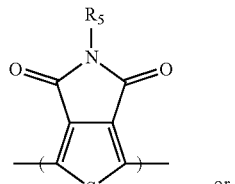

or

(44) 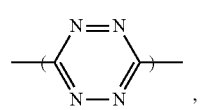

in which each of X and Y, independently, is $CH_2$, O, or S; each of $R_1$ and $R_2$, independently, COR, COOR, CO—N(RR'), $C_1$-$C_{20}$ perfluoroalkyl, CN, or $SO_3R$; in which each of R or R', independently, is H, $C_1$-$C_{24}$ alkyl, aryl, heteroaryl, $C_3$-$C_{24}$, cycloalkyl, or $C_3$-$C_{24}$ heterocycloalkyl; and each of $R_3$, $R_4$, $R_5$, $R_6$, $R_7$, and $R_8$, independently, is H, halogen (e.g., F, Cl, Br, or I), $C_1$-$C_{24}$ alkyl, $C_1$-$C_{24}$ alkoxy, aryl, heteroaryl, $C_3$-$C_{24}$ cycloalkyl, $C_3$-$C_{24}$ heterocycloalkyl, COR", or COOR", in which R" is H, $C_1$-$C_{24}$ alkyl, aryl, heteroaryl, cycloalkyl, or $C_3$-$C_{24}$ heterocycloalkyl.

Organic Compound/Monomer

In one embodiment, an organic compound, also called a monomer can comprise:

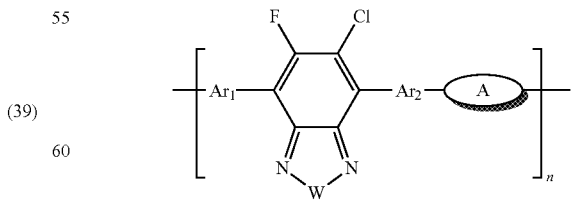

can be formed.

In this organic compound, W is selected from the group consisting of: S, Se, O, and N-Q; and Q is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring. Additionally, in this organic compound $Ar_1$ and $Ar_2$ are different and selected from aryl units.

In one embodiment of this organic compound, the fused substituted aromatic ring is fused with: H, Cl, F, CN, a straight-chain or branched carbyl, silyl, or hydrocarbyl, a branched or cyclic alkyl with 1 to 30 atoms, and an aromatic ring.

In another embodiment of the organic compound, $Ar_1$ and $Ar_2$ can be the same, $Ar_1$ and $Ar_2$ can be different, or one $Ar_1$ or $Ar_2$ can be H.

In this embodiment, n can be any number of organic compounds necessary to produce an organic photovoltaic polymer from n=2 to n=1,000, 10,000, even 100,000.

In yet another embodiment, $Ar_1$, $Ar_2$ and

Ⓐ are independently selected from:

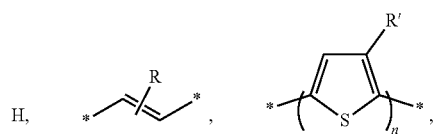

,

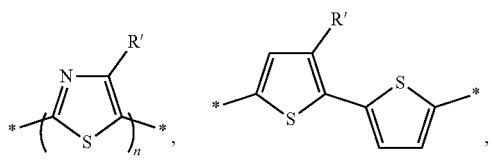

,

-continued

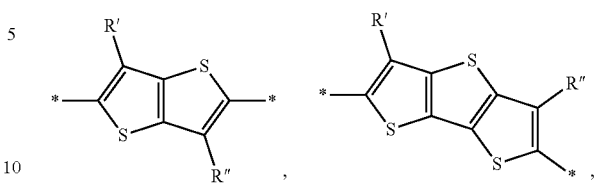

,

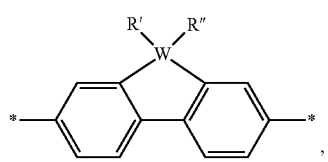

,

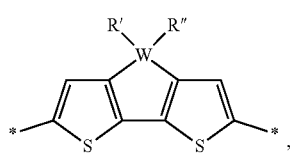

,

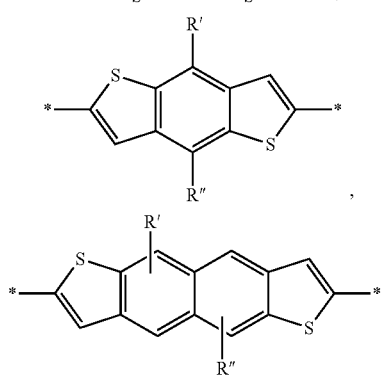

,

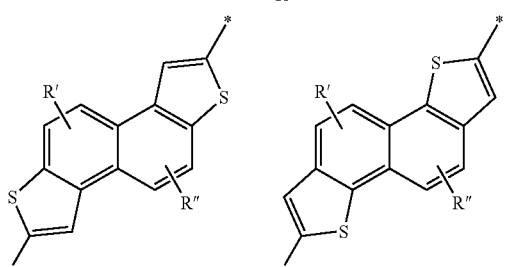

,

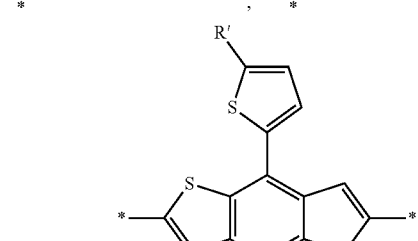

,

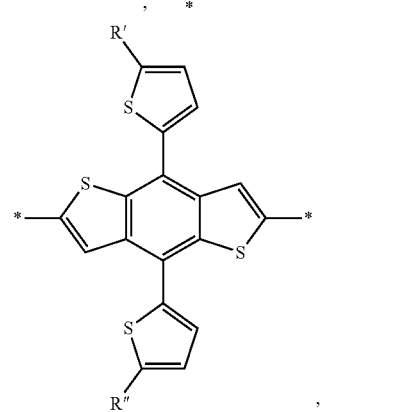

,

23
-continued
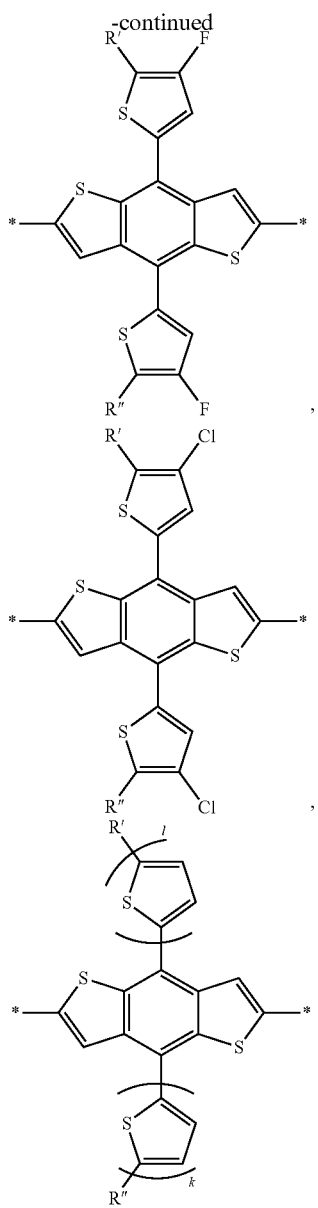
In yet another embodiment, the organic compounds can be
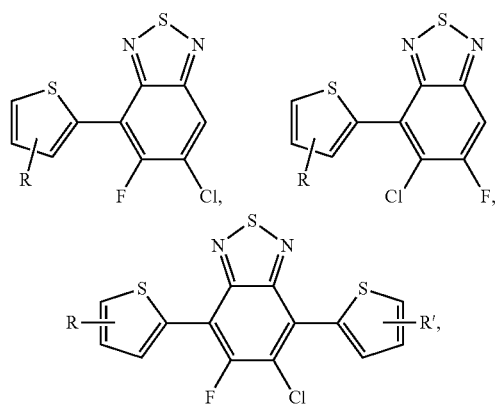
24
-continued
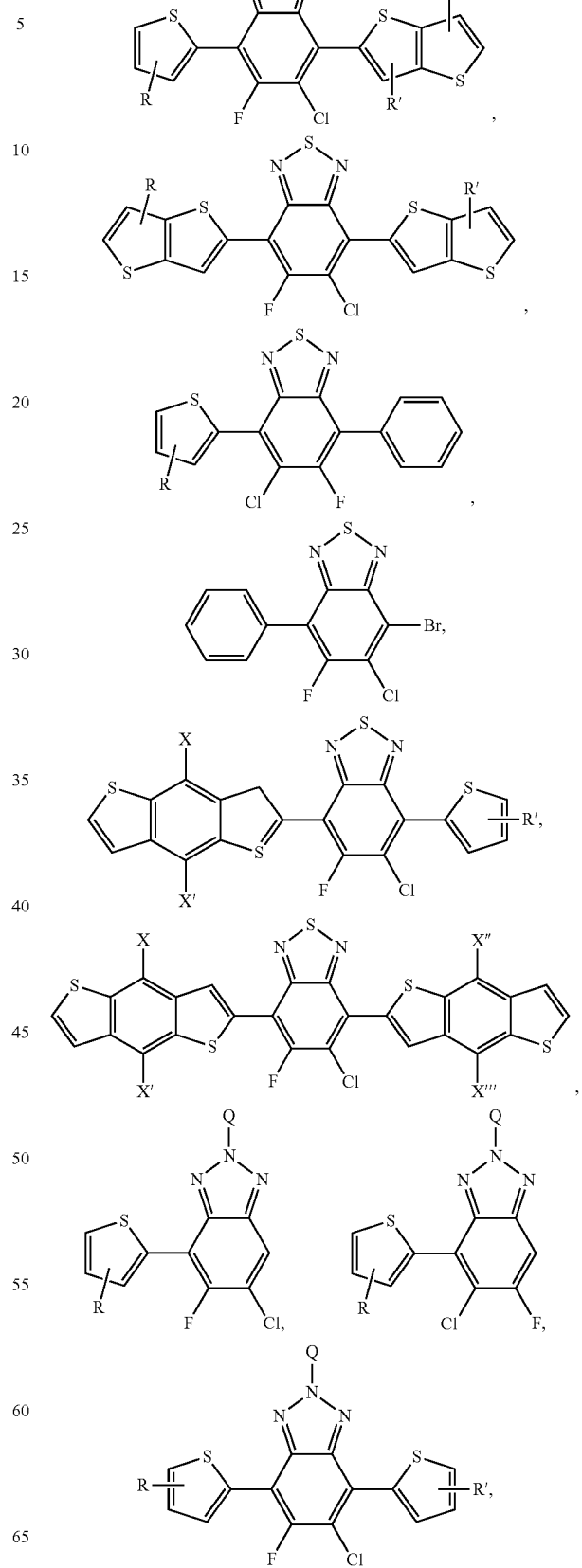

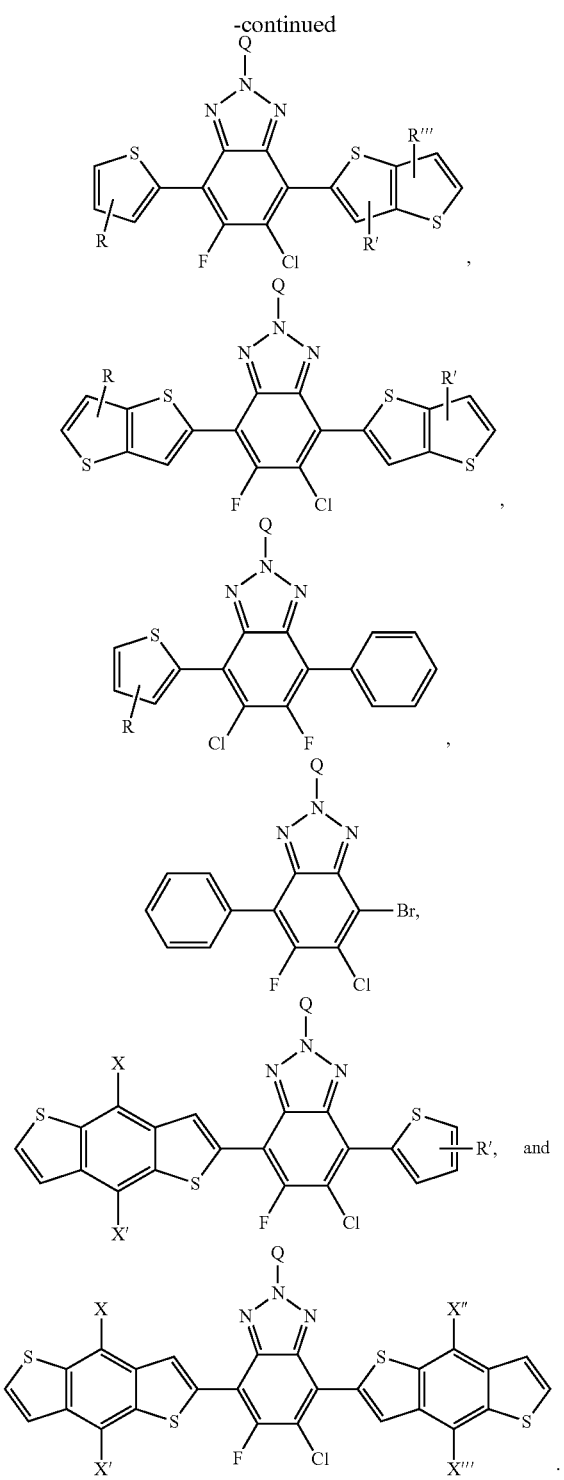

In this embodiment: W could be S, Se, O, or N-Q; Q a straight-chain or branched carbyl, silyl, or hydrocarbyl, a branched or cyclic alkyl with 1 to 30 atoms, a fused substituted aromatic ring, and a fused unsubstituted aromatic ring. The fused substituted aromatic rings can fused with H, Cl, F, CN, a straight-chain or branched carbyl, silyl, or hydrocarbyl, a branched or cyclic alkyl with 1 to 30 atoms, and an aromatic ring.

R', R", X, X', X", X'" can be independently selected from the group consisting of: H, Cl, F, CN, an alkyl group, an alkoxy group, an aryl group, a $C_{6-20}$ alkyl group, a —O—$C_{6-20}$ alkyl group, a —O—$C_{6-20}$ alkenyl group, a —O—$C_{6-20}$ haloalkyl group, a —S—$C_{6-20}$ alkyl group, a —S—$C_{6-20}$ alkenyl group, a —S—$C_{6-20}$ haloalkyl group, a -thienyl-$C_{6-20}$ alkyl group, a -thienyl-$C_{6-20}$ alkenyl group, and a -thienyl-$C_{6-20}$ haloalkyl group.

Monomer Synthesis

From the above constitutional units of comonomers, any conventionally known coupling reaction can be used to make monomers. Examples of different coupling reactions that can be used include, Wurtz reaction, Glaser coupling, Ullman reaction, Gomberg-Bachmann reaction, Cadiot-Chodkiewicz coupling, Pinacol coupling reaction, Castro-Stephens coupling, Gilman reagent coupling, Cassar reaction, Kumada coupling, Heck reaction, Sonogashira coupling, Negishi coupling, Stile coupling, Suzuki reaction, Hiyama coupling, Buchwald-Hartwig reaction, Fukuyama coupling, Liebeskind-Srogl coupling, Direct Heteroarylation and MacMillan coupling.

Figure 2:
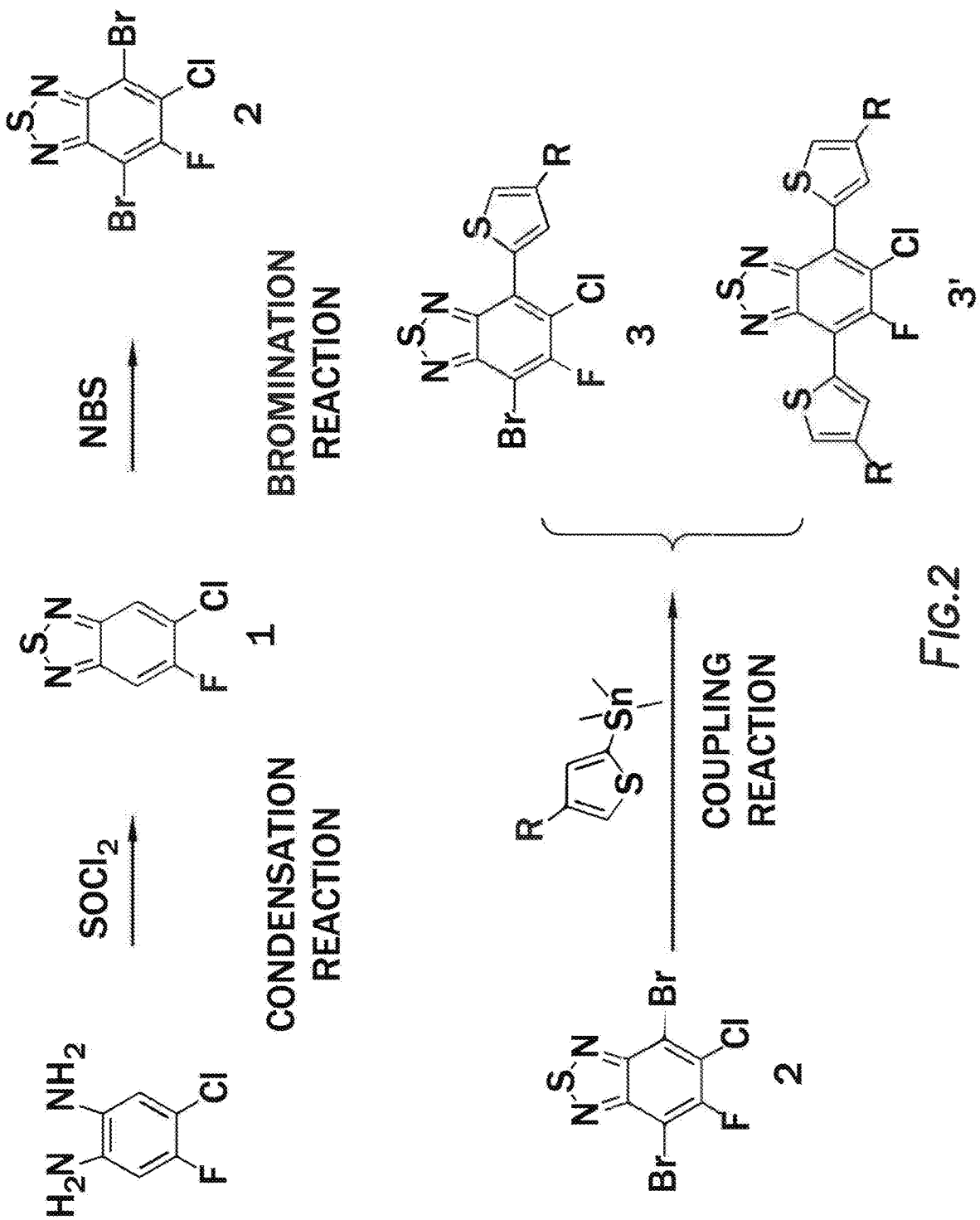
FIG. 2 depicts the creation of 4,7-dibromo-5-chloro-6-fluorobenzo[c][1,2,5]thiadiazole.

For examples, as shown in FIG. 2,

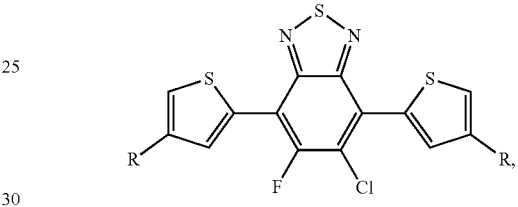

4,7-dibromo-5-chloro-6-fluorobenzo[c][1,2,5]thiadiazole can by created from 4-chloro-5-fluorobenzene-1,2-diamine, as shown below.

Figure 3:
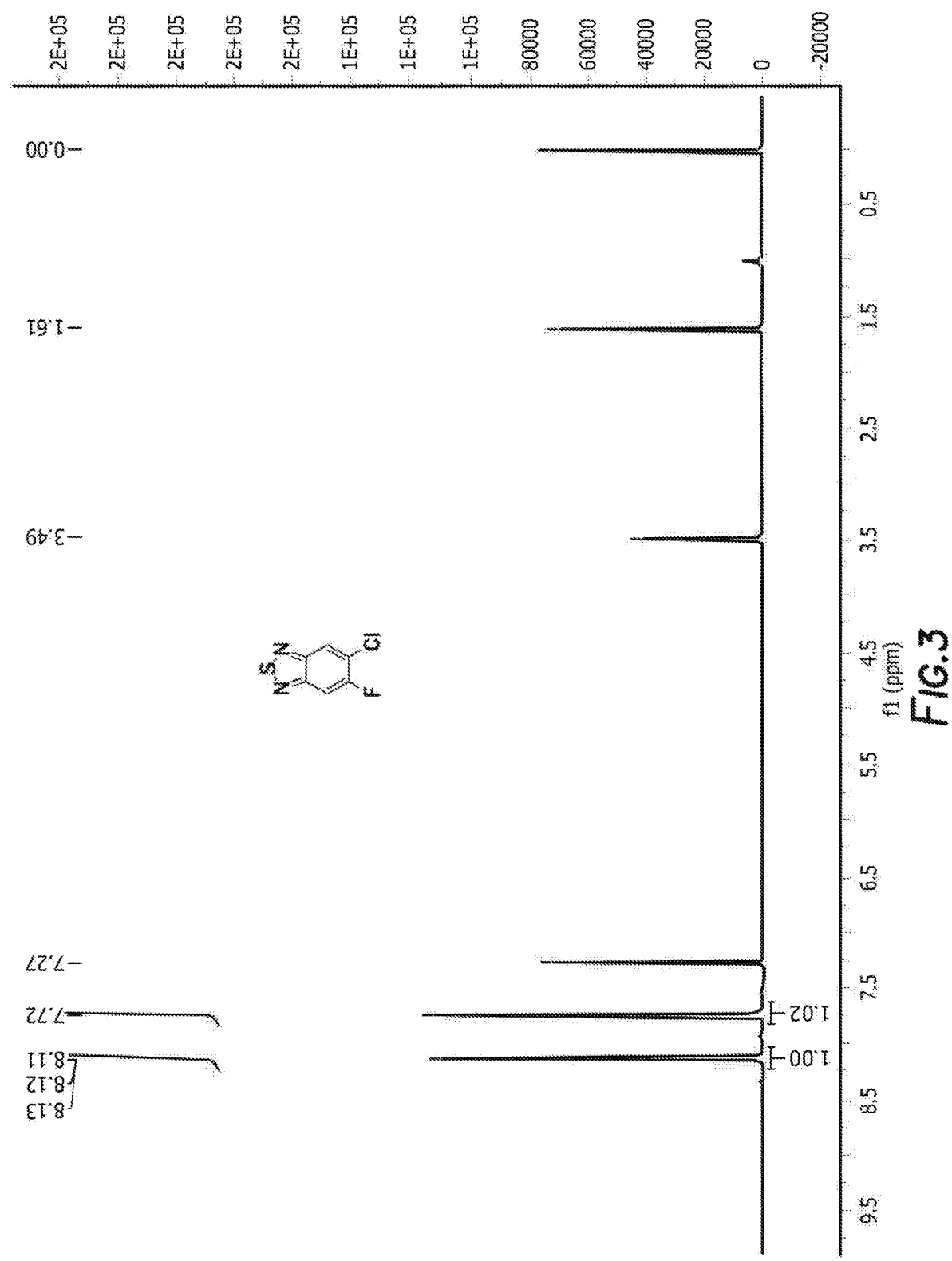
FIG. 3 depicts the spectra of 4,7-dibromo-5-chloro-6-fluorobenzo[c][1,2,5]thiadiazole.
Figure 4:
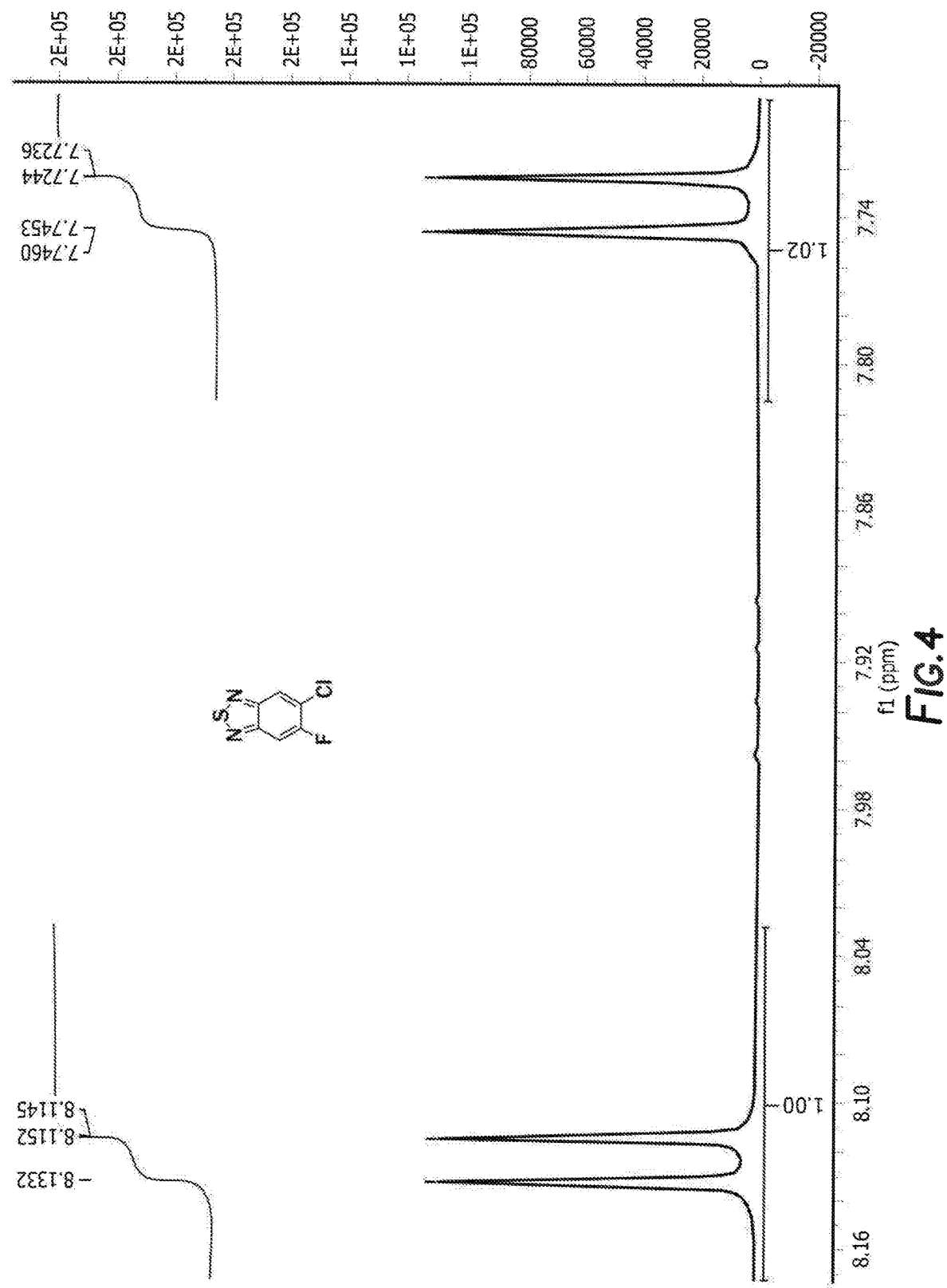
FIG. 4 depicts the spectra of 4,7-dibromo-5-chloro-6-fluorobenzo[c][1,2,5]thiadiazole.
Figure 5:
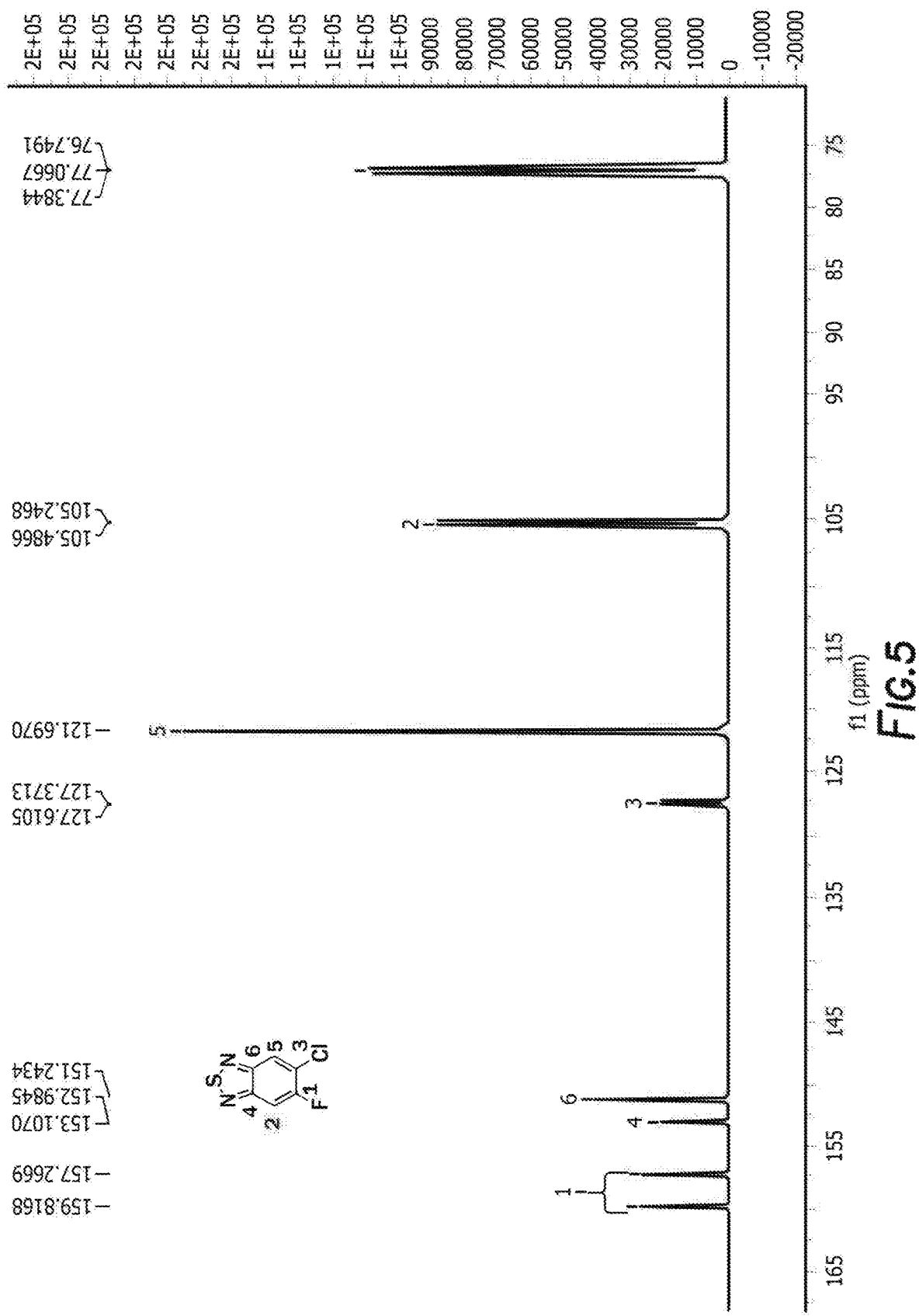
FIG. 5 depicts the spectra of 4,7-dibromo-5-chloro-6-fluorobenzo[c][1,2,5]thiadiazole.
Figure 6A:
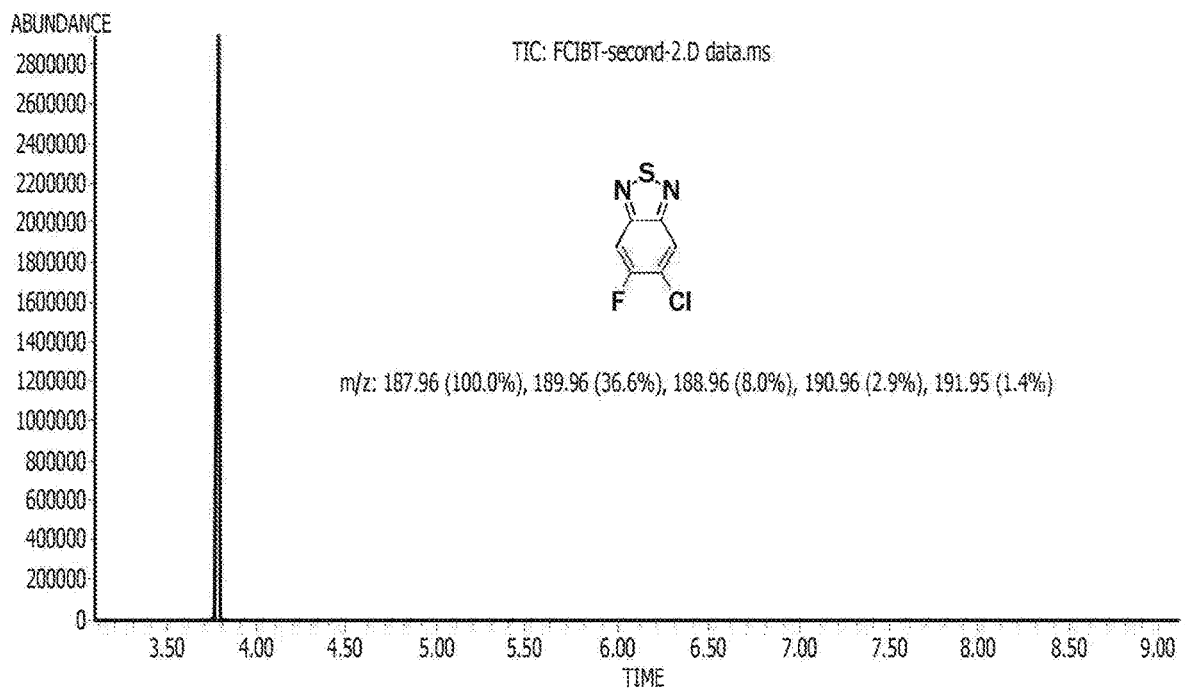
FIG. 6a depicts the spectra of 4,7-dibromo-5-chloro-6-fluorobenzo[c][1,2,5]thiadiazole.
Figure 6B:
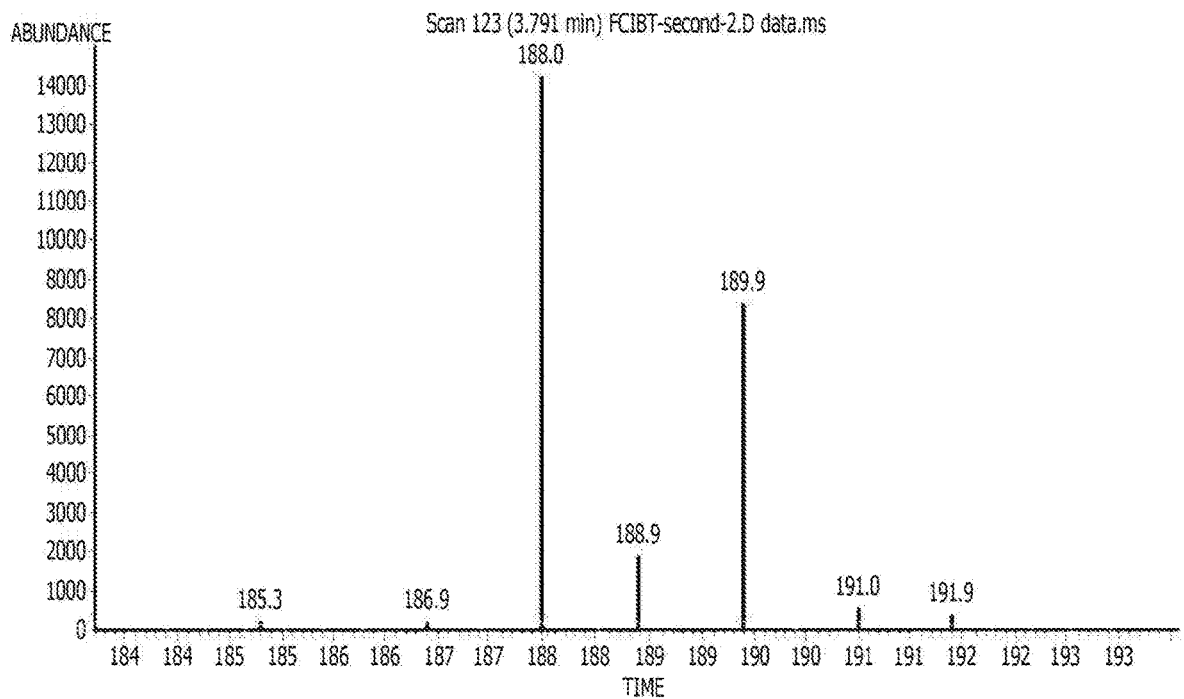
FIG. 6b depicts the spectra of 4,7-dibromo-5-chloro-6-fluorobenzo[c][1,2,5]thiadiazole.

To begin the process, one must first synthesize 4,7-dibromo-5-chloro-6-fluorobenzo[c][1,2,5]thiadiazole. The process begins by taking 4-chloro-5-fluorobenzene-1,2-diamine and flushing it with argon. Subsequently, triethylamine was added as solvent and then dichloromethane and thionyl chloride. The resulting mixture was stirred at and cooled down to room temperature and then quenched slowly with water. The mixture was extracted with dichloromethane. The dichloromethane layer was dried over anhydrous MgSO4 before the solvent was removed. The results white solid was further purified by flash column with hexane/dichloromethane mixture as eluent. White crystal 4,7-dibromo-5-chloro-6-fluorobenzo[c][1,2,5]thiadiazole was obtained as product. The H NMRs are shown in FIGS. 3 and 4, and C NMR shown in FIG. 5 with the GC-MS as shown in FIGS. 6a and 6b.

Figure 7:
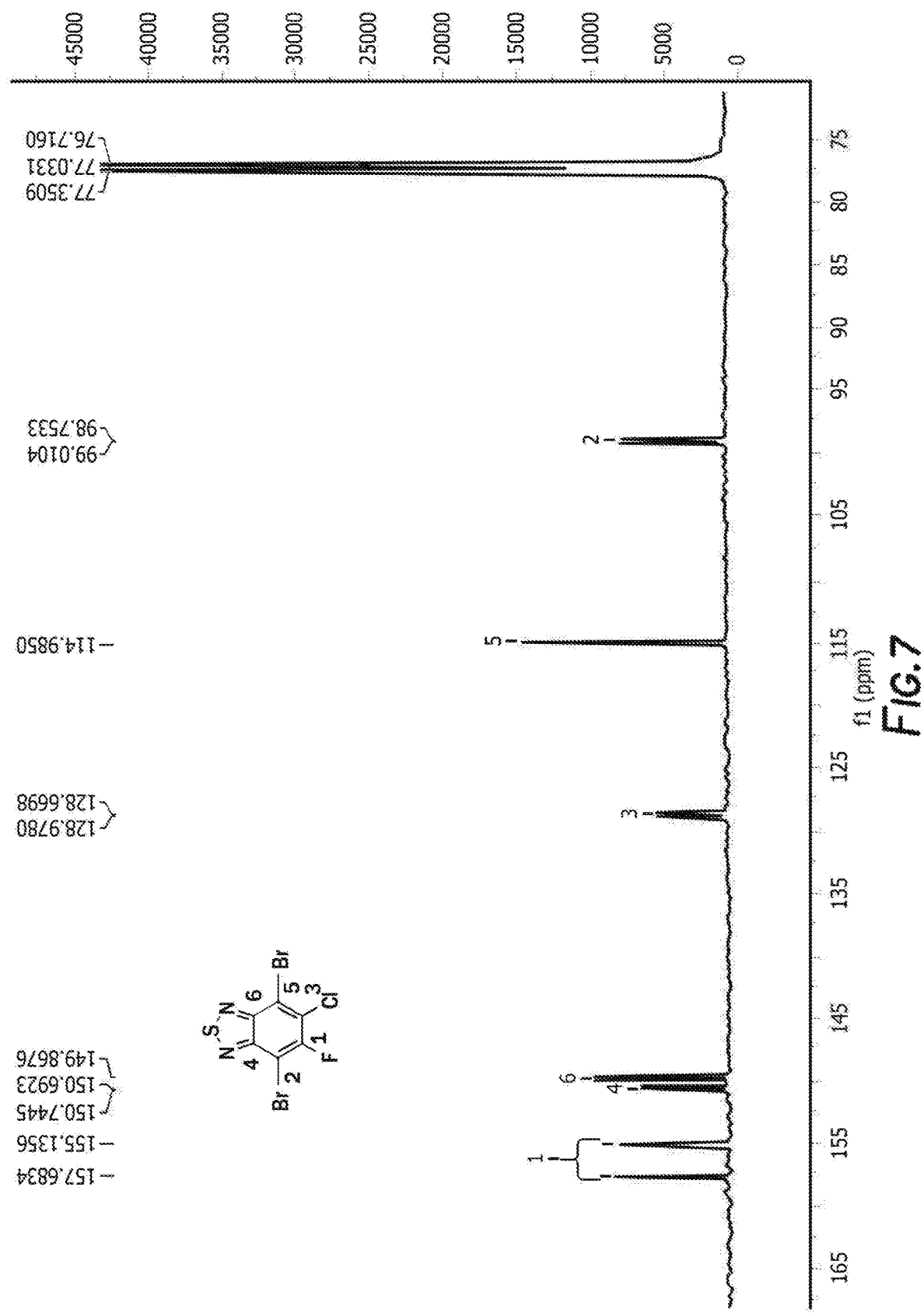
FIG. 7 depicts the spectra of 4,7-dibromo-5-chlorobenzo[c][1,2,5]thiadiazole.
Figure 8:
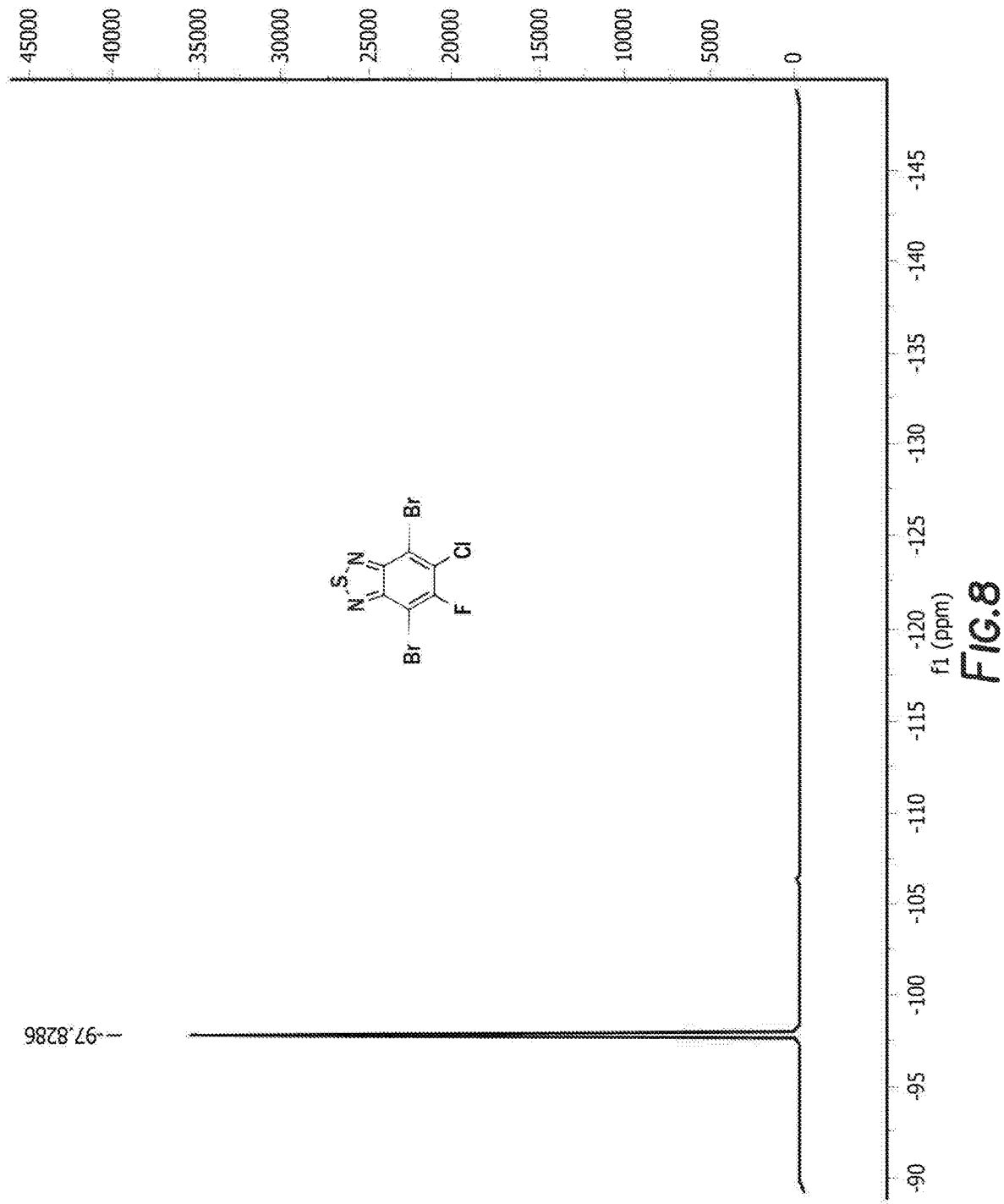
FIG. 8 depicts the spectra of 4,7-dibromo-5-chlorobenzo[c][1,2,5]thiadiazole.
Figure 9A:
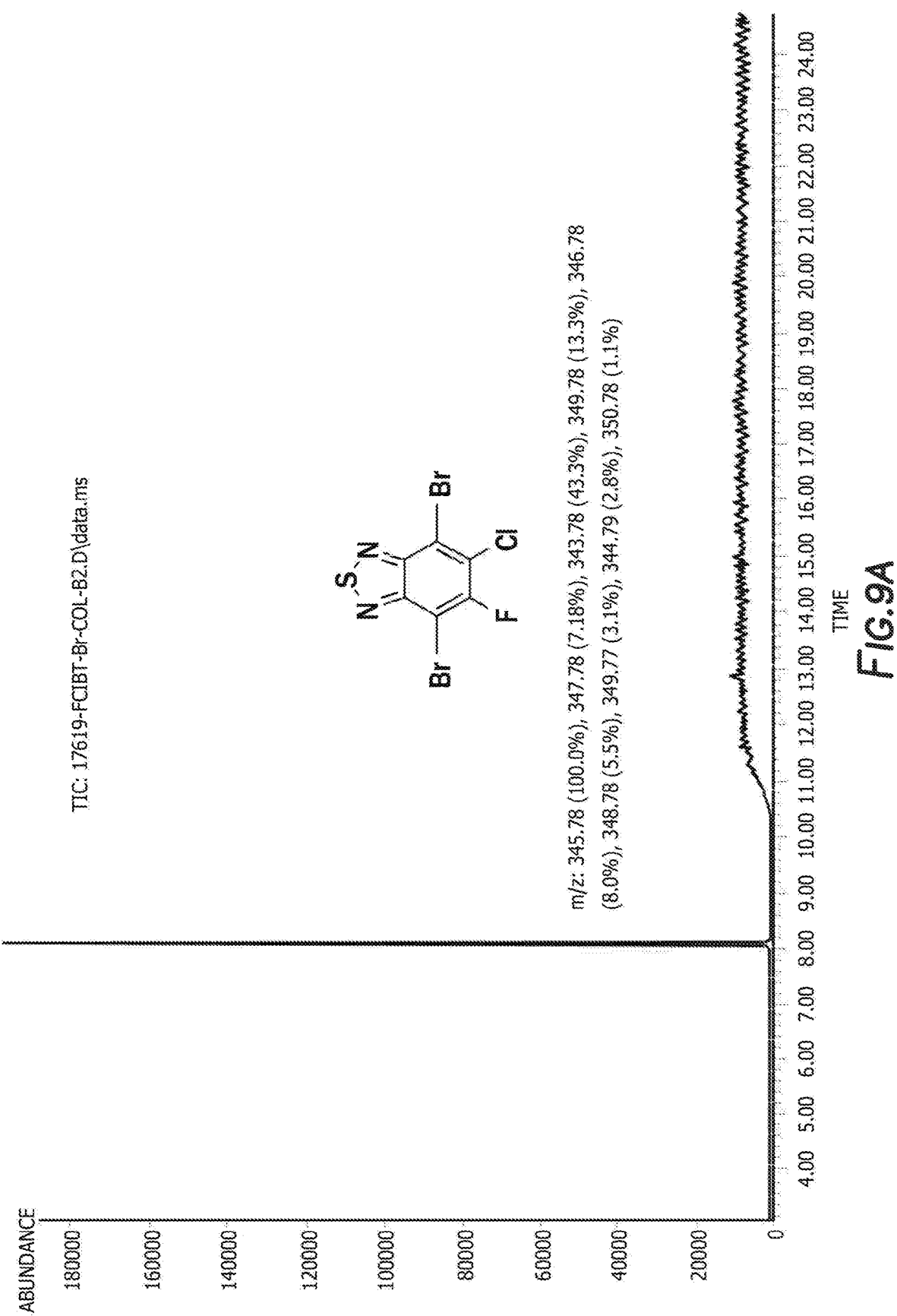
FIG. 9a depicts the spectra of 4,7-dibromo-5-chlorobenzo[c][1,2,5]thiadiazole.
Figure 9B:
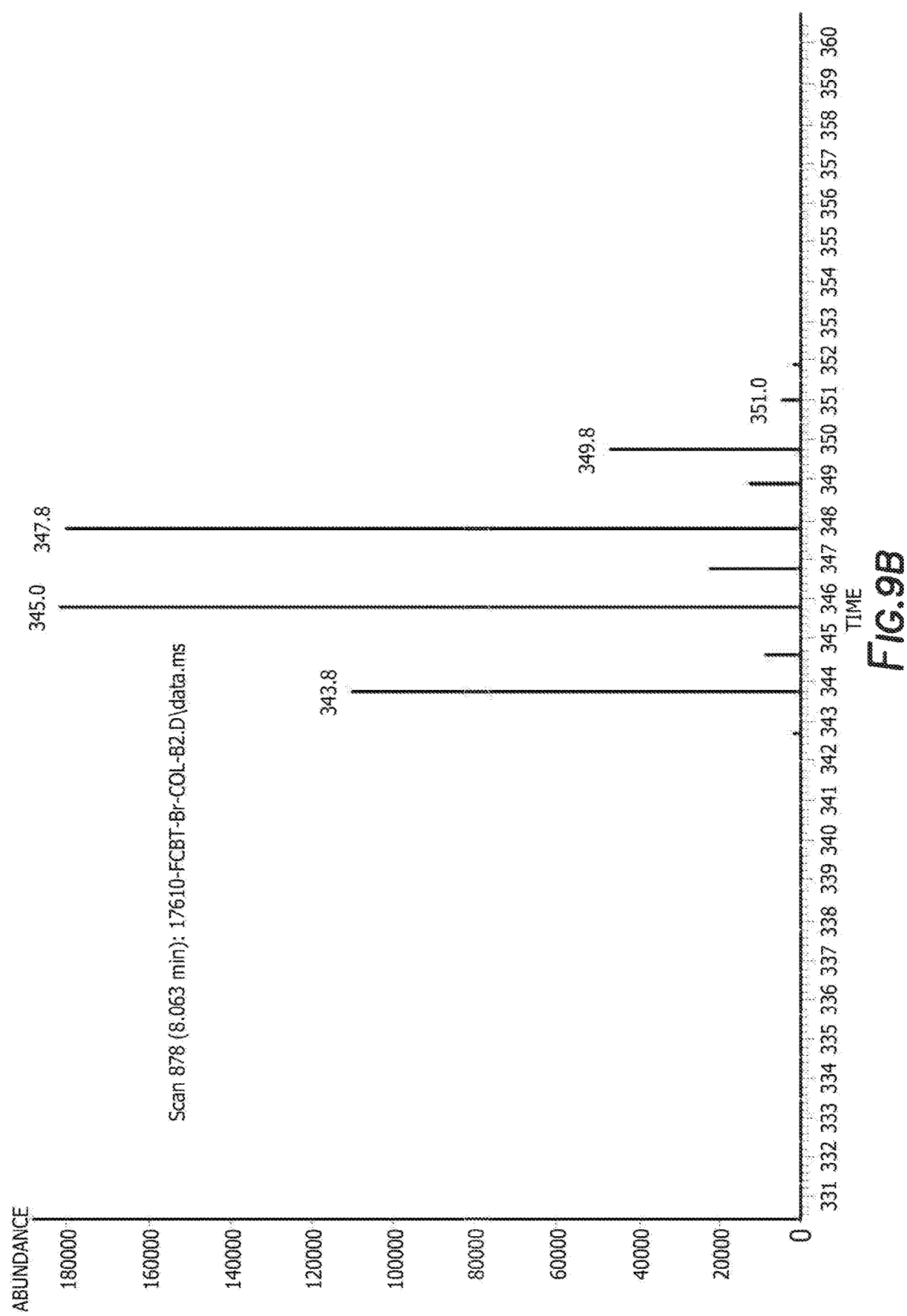
FIG. 9b depicts the spectra of 4,7-dibromo-5-chlorobenzo[c][1,2,5]thiadiazole.

The next step of the process is the synthesis of 4,7-dibromo-5-chlorobenzo[c][1,2,5]thiadiazole. 5-chloro-6-fluoro-2,1,3-benzothiadiazole was put into a Schlenk flask and flushed with Argon before sulfuric acid and N-Bromosuccinimide was added. The reaction was stirred, cooled and, extracted out with chloroform. The organic layer was dried with anhydrous $MgSO_4$ before the removal of solvent. The resulting solid was purified by column with hexane/dichloromethane as eluent. The C NMRs of 4,7-dibromo-5-chlorobenzo[c][1,2,5]thiadiazole are shown in FIG. 7 with the F NMR shown in FIG. 8. GC-MS of 4,7-dibromo-5-chlorobenzo[c][1,2,5]thiadiazole are shown in FIGS. 9a and 9b.

Figure 10:
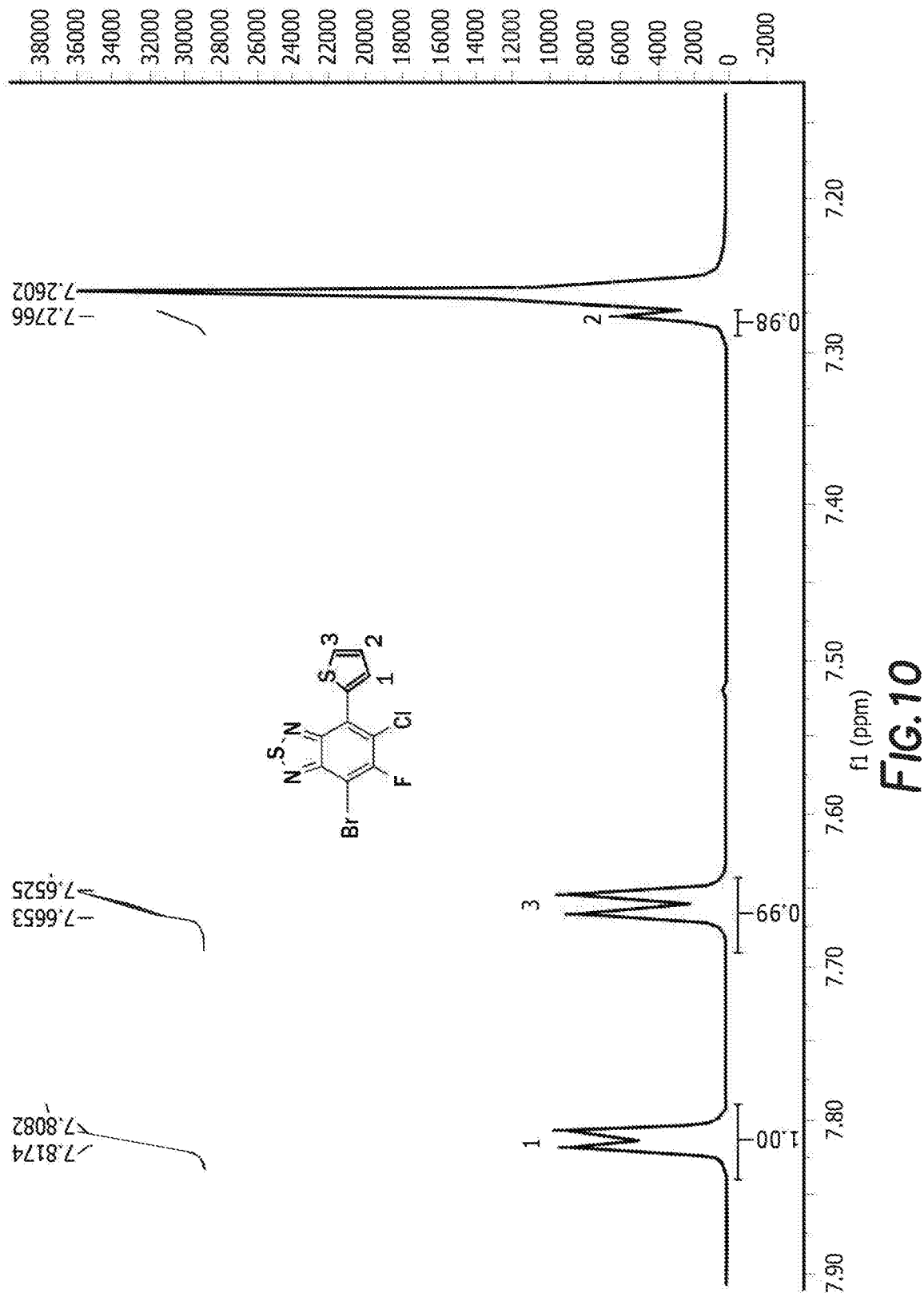
FIG. 10 depicts the spectra of 4-bromo-6-chloro-5-fluoro-7-(thiophen-2-yl)benzo[c][1,2,5]thiadiazole 3.
Figure 11:
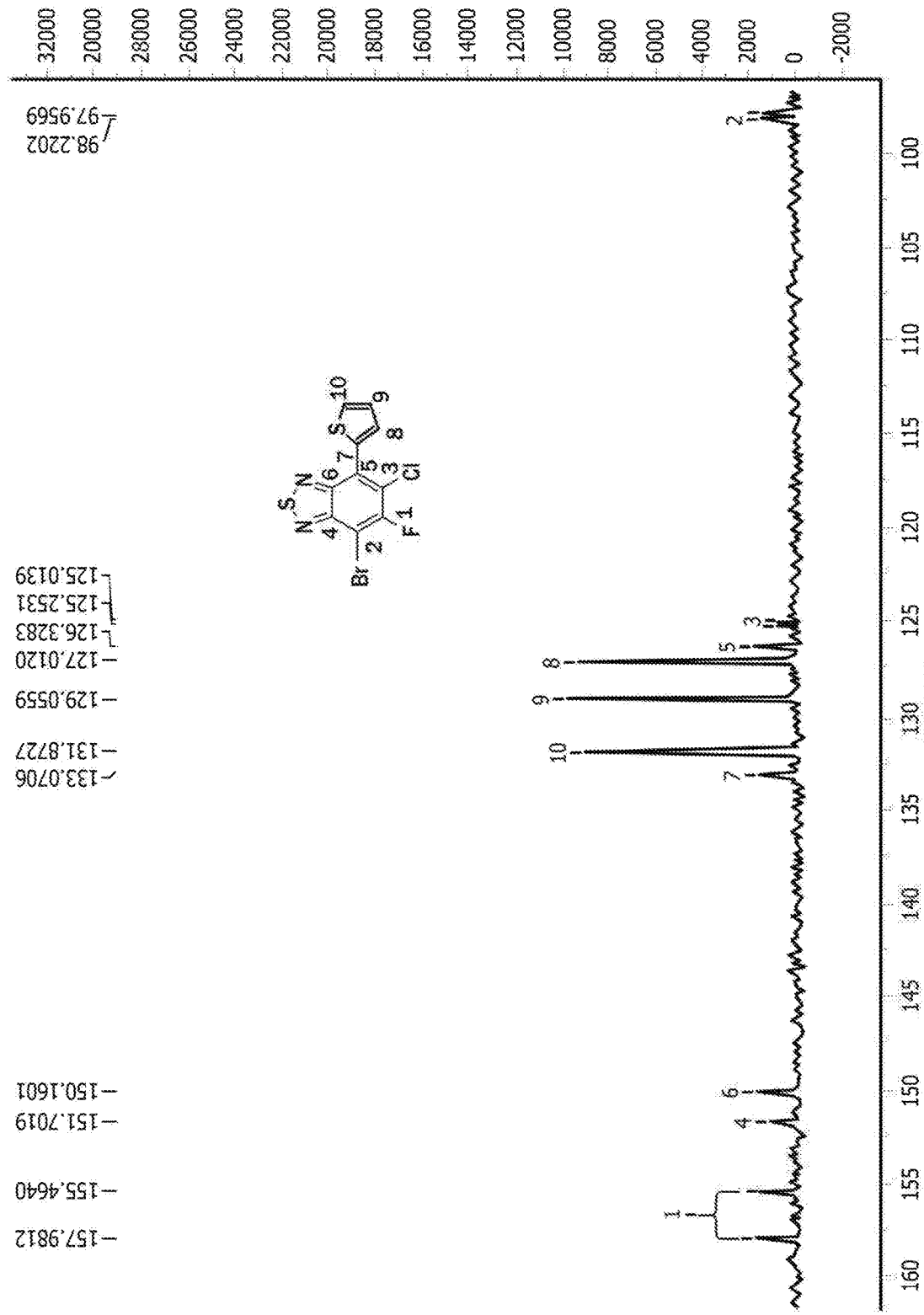
FIG. 11 depicts the spectra of 4-bromo-6-chloro-5-fluoro-7-(thiophen-2-yl)benzo[c][1,2,5]thiadiazole 3.
Figure 12:
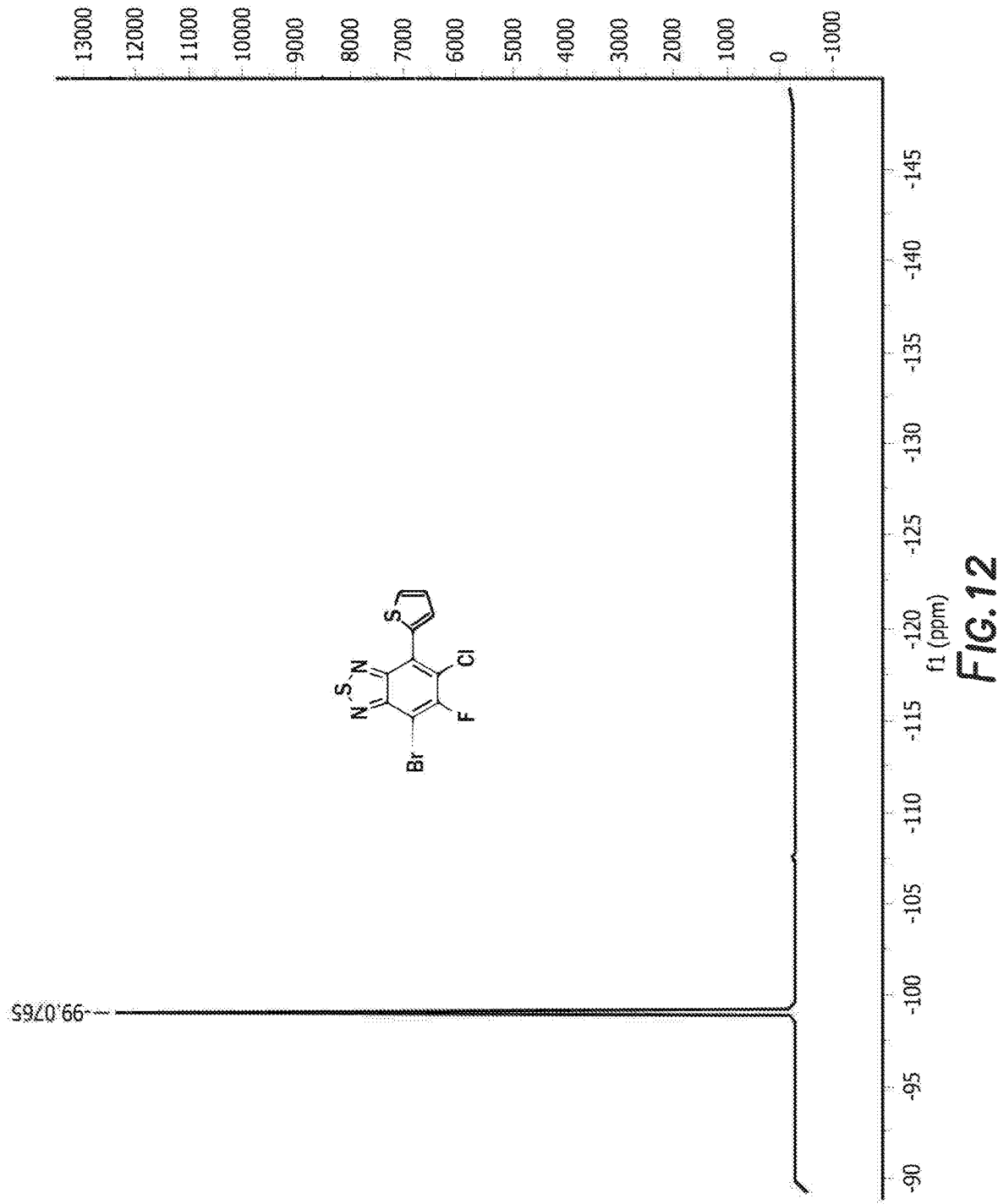
FIG. 12 depicts the spectra of 4-bromo-6-chloro-5-fluoro-7-(thiophen-2-yl)benzo[c][1,2,5]thiadiazole 3.
Figure 13A:
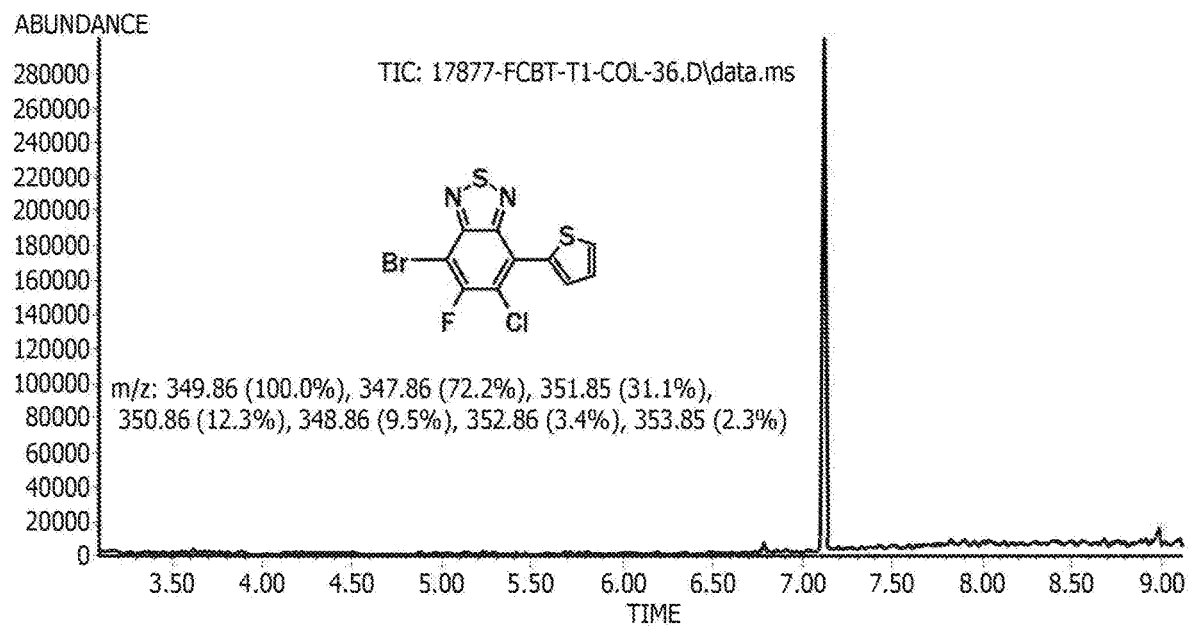
FIG. 13a depicts the spectra of 4-bromo-6-chloro-5-fluoro-7-(thiophen-2-yl)benzo[c][1,2,5]thiadiazole 3.
Figure 13B:
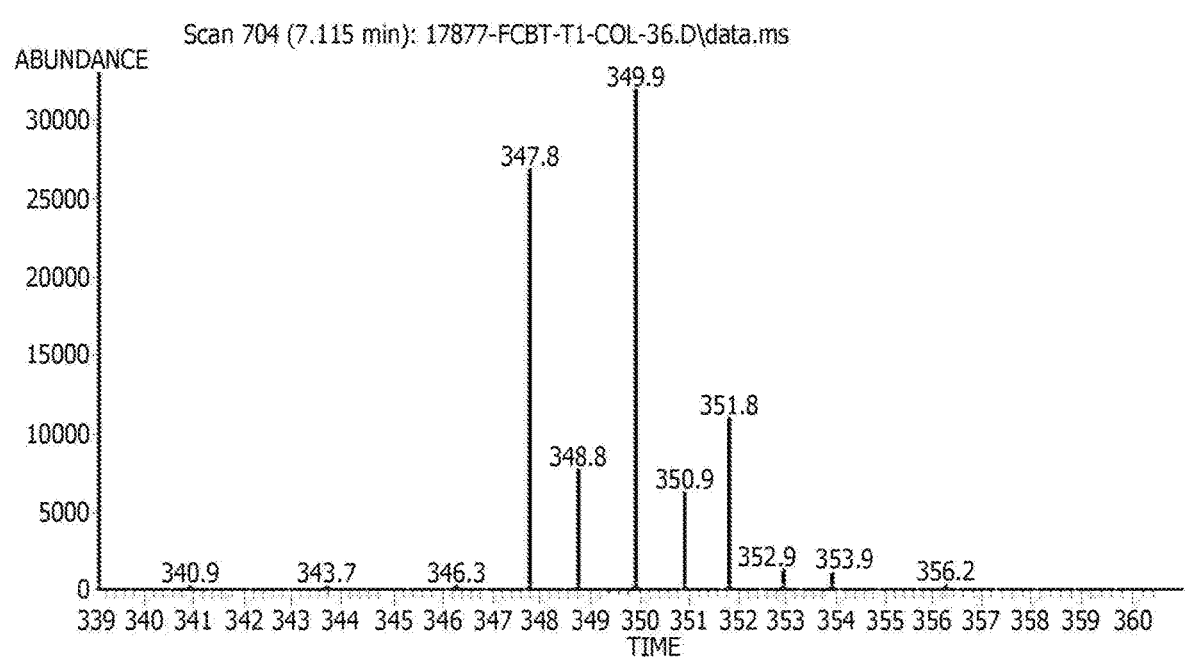
FIG. 13b depicts the spectra of 4-bromo-6-chloro-5-fluoro-7-(thiophen-2-yl)benzo[c][1,2,5]thiadiazole 3.
Figure 14:
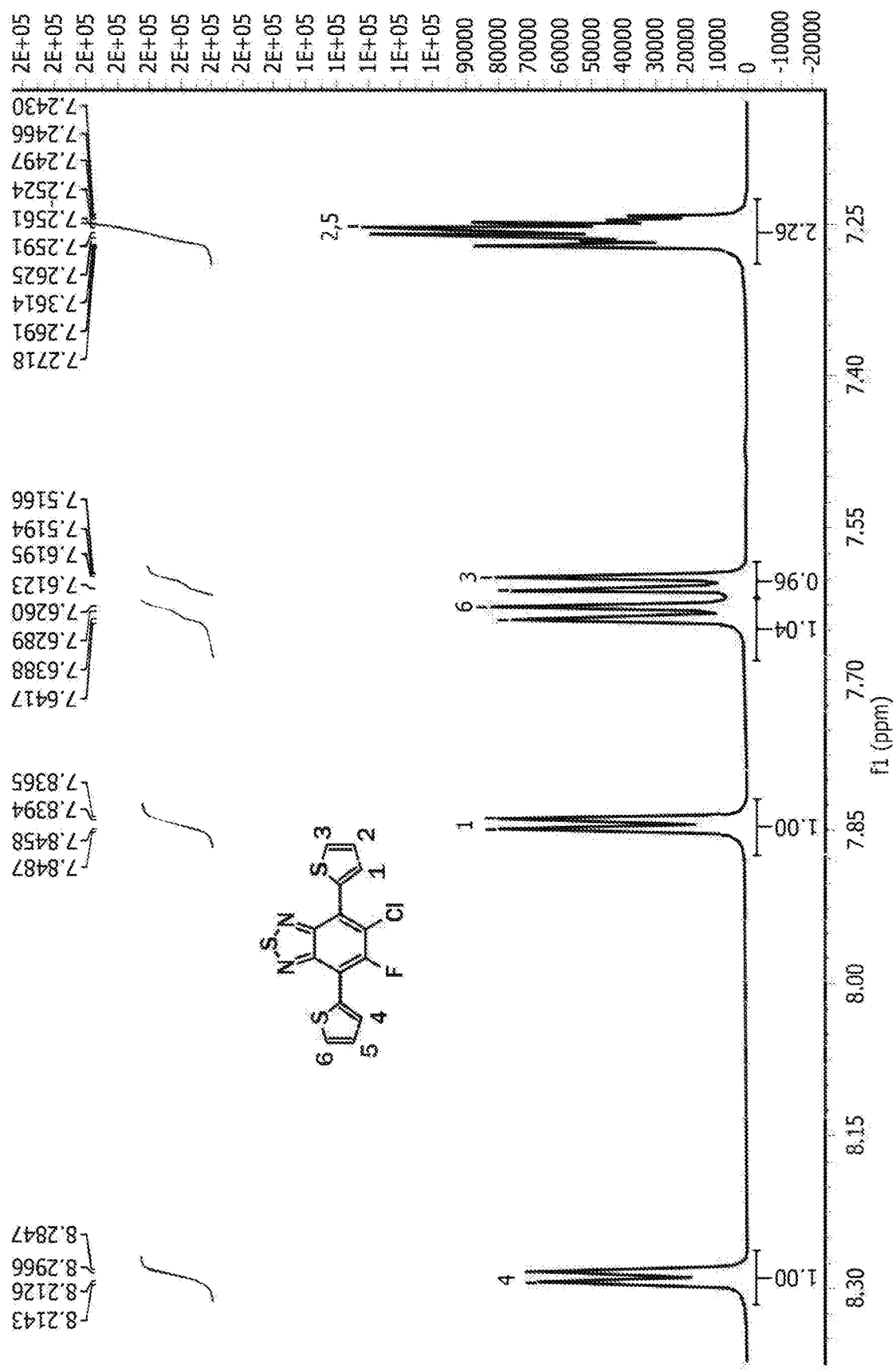
FIG. 14 depicts the spectra of 5-chloro-6-fluoro-4,7-di(thiophen-2-yl)benzo[c][1,2,5]thiadiazole 3'.

The next step is the synthesis of 4-bromo-6-chloro-5-fluoro-7-(thiophen-2-yl)benzo[c][1,2,5]thiadiazole 3 and 5-chloro-6-fluoro-4,7-di(thiophen-2-yl)benzo[c][1,2,5]thiadiazole 3'. 4,7-dibromo-5-chloro-6-fluoro-2,1,3-benzothiadiazole, tributyl(thiophen-2-yl)stannane, and tetrakis(triphenylphosphine) palladium are first combined with anhydrous dimethylformamide. The reaction is then heated and cooled down to room temperature. The solvent was removed by rotary evaporator and the resulting residue was washed with hot methanol before purification by silica gel column. Recrystallization from the mixture solvent of IPA/methanol finally offered orange crystal as product 4-bromo-6-chloro-5-fluoro-7-(thiophen-2-yl)benzo[c][1,2,5]thiadiazole 3 and 5-chloro-6-fluoro-4,7-di(thiophen-2-yl)benzo[c][1,2,5]thiadiazole 3'. For 4-bromo-6-chloro-5-fluoro-7-(thiophen-2-yl)benzo[c][1,2,5]thiadiazole 3 the H NMR is shown in FIG. 10, C NMR in FIG. 11, F NMR in FIG. 12, and GC-MS shown in FIGS. 13a and 13b. For 5-chloro-6-fluoro-4,7-di(thiophen-2-yl)benzo[c][1,2,5]thiadiazole 3' the H NMR is shown in FIG. 14, C NMR in FIG. 15, and GC-MS shown in FIGS. 16a and 16b.

Figure 17:
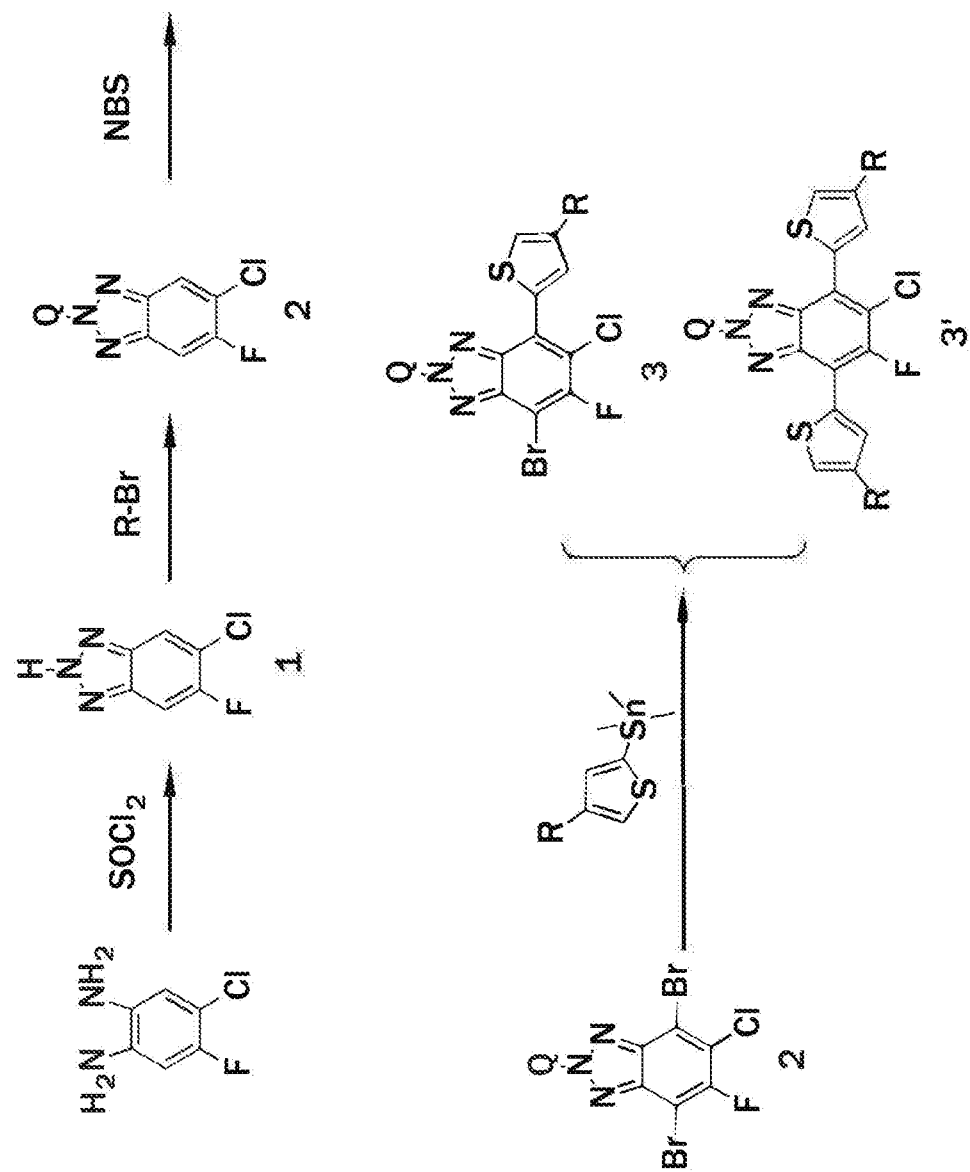
FIG. 17 depicts a reaction mechanism.

As shown in FIG. 17,

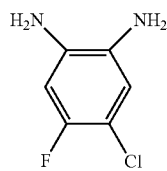

can be used to create both

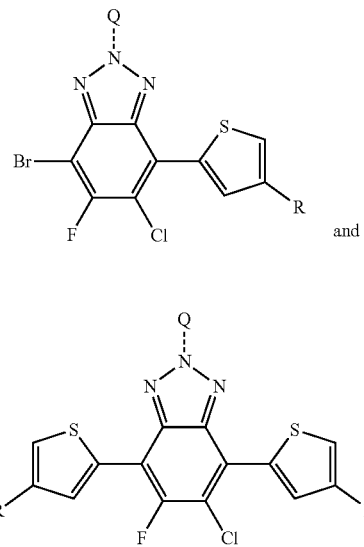

Synthesis of 4-bromo-6-chloro-5-fluoro-7-(4-(alkyl)thiophen-2-yl)benzo[c][1,2,5]thiadiazole 4,7-dibromo-5-chloro-6-fluorobenzo[c][1,2,5]thiadiazole (0.85 g, 2.45 mmol), trimethyl[4-(alkyl)thiophen-2-yl]stannane and tetrakis(triphenylphosphine)palladium(0) Pd(PPh$_3$)$_4$ were combined. After the flask was degassed anhydrous dimethylformamide (DMF) was injected. The reaction was heated and cooled down to room temperature. The toluene solvent was removed under vacuum and the resulting residue was purified by silica gel column chromatography with pure hexane as the eluent. Recrystallization from the solvent mixture of isopropanol/hexane (v/v, 4:1) afforded red crystals as the product (1.02 g, 66.0%). The $^1$H NMR spectrum is shown in FIG. 13.

Figure 15:
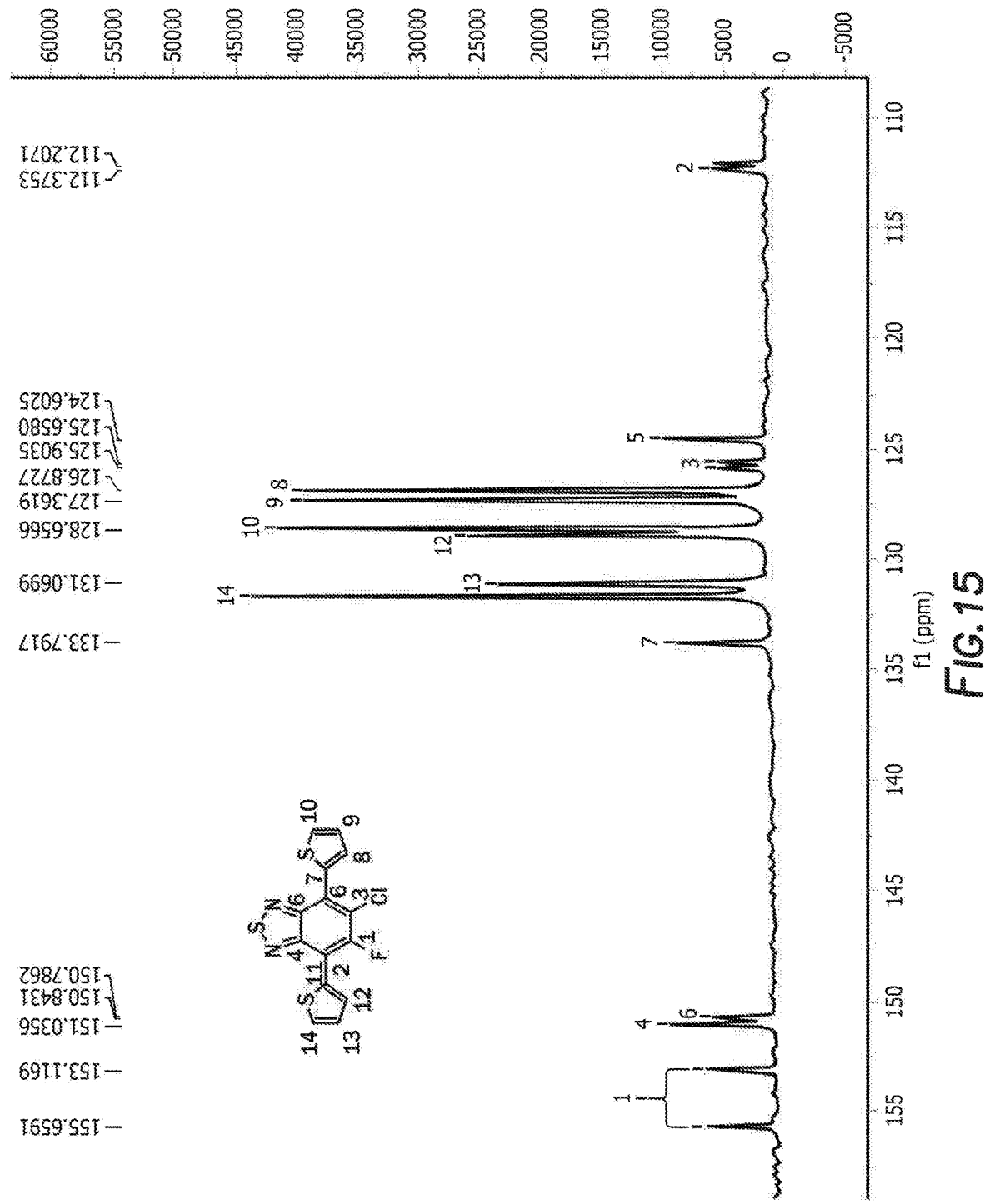
FIG. 15 depicts the spectra of 5-chloro-6-fluoro-4,7-di(thiophen-2-yl)benzo[c][1,2,5]thiadiazole 3'.
Figure 16A:
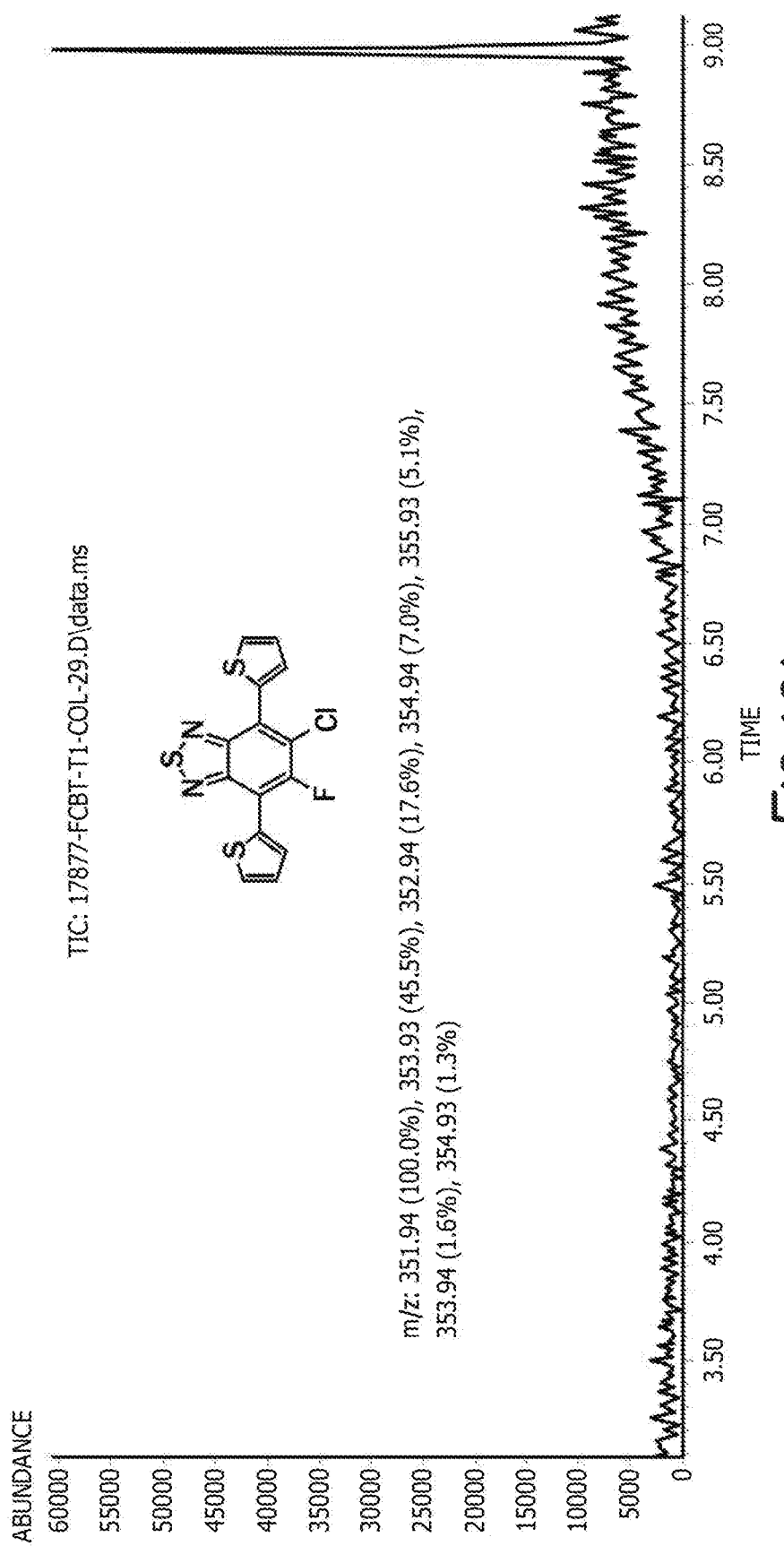
FIG. 16a depicts the spectra of 5-chloro-6-fluoro-4,7-di(thiophen-2-yl)benzo[c][1,2,5]thiadiazole 3'.

Synthesis of 4-(5-bromo-4-(alkyl)thiophen-2-yl)-7-(5-bromothiophen-2-yl)-5-chloro-6-fluorobenzo[c][1,2,5]thiadiazole:

4-bromo-6-chloro-5-fluoro-7-(4-(alkyl)thiophen-2-yl) benzo[c][1,2,5]thiadiazole was added followed by anhydrous THF. The solution was cooled and N-bromosuccinimide was added in portions. The reaction was quenched by the addition of a saturated potassium carbonate solution and extracted with hexane. The combined organic layer was dried over anhydrous MgSO$_4$. After the removal of solvent under vacuum, the resulting mixture was subjected to column chromatography purification with hexane as the eluent. Yellow crystals (0.5 g, 43.1%) were obtained after recrystallization from iso-propanol/hexane (v/v, 1:1). The $^1$H and $^{13}$C NMR spectra are shown in FIGS. 14 and 15, respectively.

Synthesis of 4,7-bis(5-bromo-4-(alkyl)thiophen-2-yl)-5-chloro-6-fluorobenzo[c][1,2,5]thiadiazole.

4,7-dibromo-5-chloro-6-fluorobenzo[c][1,2,5]thiadiazole, trimethyl[4-(alkyl)thiophen-2-yl]stannane, tris(dibenzylideneacetone)dipalladium(0) (Pd$_2$(dba)$_3$), and tri(o-tolyl) phosphine (P(o-tol)$_3$) were combined. After the flask was degassed, anhydrous toluene was injected. The reaction was heated and cooled down to room temperature. The toluene solvent was removed under vacuum and the resulting residue was purified by silica gel column chromatography with pure hexane as the eluent. Recrystallization from the solvent mixture of isopropanol/hexane (v/v, 4:1) afforded red crystals as the product (2.46 g, 93.0%). The $^1$H NMR spectrum is shown in FIG. 13.

Synthesis of 4,7-bis(5-bromo-4-(alkyl)thiophen-2-yl)-5-chloro-6-fluorobenzo[c][1,2,5]thiadiazole: 4,7-bis(5-bromo-4-(alkyl)thiophen-2-yl)-5-chloro-6-fluorobenzo[c][1,2,5] thiadiazole (2.35 g, 2.571 mmol) was added to a 100-mL Schlenk flask followed by 35 mL of anhydrous THF. The solution was cooled to −78° C. and N-bromosuccinimide (0.961 g, 5.4 mmol) was added in portions. The reaction was stirred overnight at room temperature. The reaction was quenched by the addition of a saturated potassium carbonate solution and extracted with hexane. The combined organic layer was dried over anhydrous MgSO$_4$. After the removal of solvent under vacuum, the resulting mixture was subjected to column chromatography purification with hexane as the eluent. Yellow crystals (2.46 g, 89.3%) were obtained after recrystallization from iso-propanol/hexane (v/v, 1:1). The $^1$H and $^{13}$C NMR spectra are shown in FIGS. 14 and 15, respectively.

Synthesis of Polymer 4-bromo-7-[5-bromo-4-(alkyl)thiophen-2-yl]-6-chloro-5-fluoro-2,1,3-benzothiadiazole, (3,3'-difluoro-[2,2'-bithiophene]-5,5'-diyl)bis(trimethylstannane), [4-(2-hexyldecyl)-5-[5-(trimethylstannyl)thiophen-2-yl]thiophen-2-yl] trimethylstannane, Pd$^2$dba$_3$ tris(dibenzylideneacetone); dipalladium and P(o-tol)$_3$ tris(2-methylphenyl) were combined. The mixture was degassed and of anhydrous o-dichlorobenzene was injected. The solution was heated and cooled to room temperature. The product was precipitated by pouring the solution into methanol. The solid was purified by Soxhlet extraction, using acetone, hexane, dichloromethane and chloroform as the solvents. The chloroform portion contained the main product (107 mg, yield 77.8%) after reprecipitation by methanol and then dried overnight.

Anode

When used in as an organic photovoltaic device the polymer can be used in conjunction with an anode. The anode for the organic photovoltaic device can be any conventionally known anode capable of operating as an organic photovoltaic device. Examples of anodes that can be used include: indium tin oxide, aluminum, silver, carbon, graphite, graphene, PEDOT:PSS, copper, metal nanowires, $Zn_{99}InO_x$, $Zn_{98}In_2O_x$, $Zn_{97}In_3O_x$, $Zn_{95}Mg_5O_x$, $Zn_{90}Mg_{10}O_x$, and $Zn_{85}Mg_{15}O_x$.

Cathode

When used in as an organic photovoltaic device the polymer can be used in conjunction with a cathode. The cathode for the organic photovoltaic device can be any conventionally known cathode capable of operating as an organic photovoltaic device. Examples of cathodes that can be used include: indium tin oxide, carbon, graphite, graphene, PEDOT:PSS, copper, silver, aluminum, gold, metal nanowires.

Electron Transport Layer

When used in as an organic photovoltaic device the copolymer can be deposited onto an electron transport layer. Any commercially available electron transport layer can be used that is optimized for organic photovoltaic devices. In one embodiment the electron transport layer can comprise $(AO_x)_yBO_{(1-y)}$. In this embodiment, $(AO_x)_y$ and $BO_{(1-y)}$ are metal oxides. A and B can be different metals selected to achieve ideal electron transport layers. In one embodiment A can be aluminum, indium, zinc, tin, copper, nickel, cobalt, iron, ruthenium, rhodium, osmium, tungsten, magnesium, indium, vanadium, titanium and molybdenum.

In one embodiment B can be aluminum, indium, zinc, tin, copper, nickel, cobalt, iron, ruthenium, rhodium, osmium, tungsten, vanadium, titanium and molybdenum.

Examples of $(AO_x)_yBO_{(1-y)}$ include: $(SnO_x)_yZnO_{(1-y)}$, $(AlO)_yZnO_{(1-y)}$, $(AlO)_yInO_{z(1-y)}$, $(AlO_x)_ySnO_{z(1-y)}$, $(AlO_x)_yCuO_{z(1-y)}$, $(AlO_x)_yWO_{z(1-y)}$, $(InO_x)_yZnO_{(1-y)}$, $(InO_x)_ySnO_{z(1-y)}$, $(InO_x)_yNiO_{z(1-y)}$, $(ZnO_x)_yCuO_{z(1-y)}$, $(ZnO_x)_yNiO_{z(1-y)}$, $(ZnO_x)_yFeO_{z(1-y)}$, $(WO_x)_yVO_{z(1-y)}$, $(WO_x)_yTiO_{z(1-y)}$, and $(WO_x)_yMoO_{z(1-y)}$.

In an alternate embodiment, various fullerene dopants can be combined with $(AO_x)_yBO_{(1-y)}$ to make an electron transport layer for the organic photovoltaic device. Examples of fullerene dopants that can be combined include

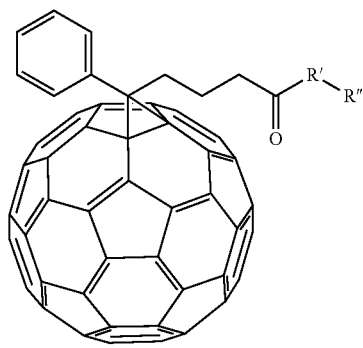

and [6,6]-phenyl-$C_{60}$-butyric-N-2-trimethylammonium ethyl ester iodide.

In the embodiment of

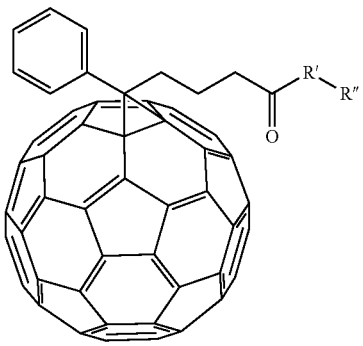

R' can be selected from either N, O, S, C, or B. In other embodiment R" can be alkyl chains or substituted alkyl chains. Examples of substitutions for the substituted alkyl chains include halogens, N, Br, O, Si, or S. In one example R" can be selected from

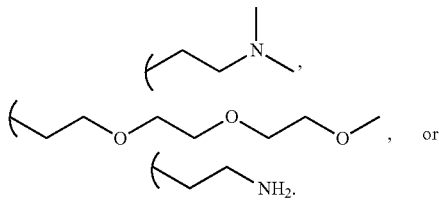

Other examples of fullerene dopants that can be used include: [6,6]-phenyl-$C_{60}$-butyric-N-(2-aminoethyl)acetamide, [6,6]-phenyl-$C_{60}$-butyric-N-triethyleneglycol ester and [6,6]-phenyl-$C_{60}$-butyric-N-2-dimethylaminoethyl ester.

Organic Photovoltaic Device Fabrication

Zinc/tin oxide (ZTO):phenyl-C60-butyric-N-(2-hydroxyethyl)acetamide (PCBNOH) sol-gel solution was prepared by dissolving zinc acetate dihydrate or tin(II) acetate in 2-methoxyethanol and ethanolamine. Specifically, the ZTO: PCBNOH sol-gel electron transport layer solution was prepared by mixing Zn(OAc)$_2$ (3.98 g), Sn(OAc)$_2$ (398 mg) and PCBNOH (20.0 mg) in 2-methoxyethanol (54 mL) with ethanolamine (996 μL). Solutions were then further diluted to 65 vol % by adding more 2-methoxyethanol and stirred for at least an hour before spin casting onto indium tin oxide substrate to form the electron transport layer.

In alternate embodiments, the formation of ZTO ([6,6]-phenyl-$C_{60}$-butyric-N-2-trimethylammonium ethyl ester iodide (PCBNMI) can be used as well. One method of forming PCBNMI can be taking [6,6]-phenyl-C60-butyric-N-2-dimethylaminoethyl ester (0.05 g, 0.052 mmol) and dissolved it in dry THF (2 mL) under argon. Iodomethane (1.5 mL) was added in one portion and the vessel was sealed. The solution is then heated to 60° C. for 18 hours. The solution was cooled and opened to allow the liquids to evaporate. The solid residue was suspended in methanol, diluted with acetone, and centrifuged. This process was repeated to produce [6,6]-phenyl-C60-butyric-N-2-trimethylammonium ethyl ester iodide as a metallic green powder (0.05 g, ~99% yield).

The polymer and the acceptor, PC$_{70}$BM, in a ratio of 1:1.2 were dissolved in chlorobenzene at the concentration of 26 mg/mL to obtain the photoactive layer solution. The solution was stirred and heated at 80° C. overnight in a nitrogen filled glove box. The next day 3.0 vol % of 1,8-diiodooctane (DIO) was added before spin-coating of the photoactive layer.

Indium tin oxide patterned glass substrates were cleaned by successive ultra-sonications in acetone and isopropanol. Each 15 min step was repeated twice, and the freshly cleaned substrates were left to dry overnight at 60° C. Preceding fabrication, the substrates were further cleaned for 1.5 min in a UV-ozone chamber and the electron transport layer was immediately spin coated on top.

Sol-gel electron transport layer solution was filtered directly onto the indium tin oxide with a 0.25 μm poly (vinylidene fluoride) filter and spin cast at 4000 rpm for 40 s. Films were then annealed at 170° C. for 15 min, and directly transferred into a nitrogen filled glove box.

The photoactive layer was deposited on the electron transport layer via spin coating at 600 rpm for 40 s with the solution and the substrate being preheated at 110° C. and directly transferred into a glass petri dish for overnight solvent annealing.

After annealing, the substrates were loaded into the vacuum evaporator where $MoO_3$ (hole transport layer) and Ag (anode) were sequentially deposited by thermal evaporation. Deposition occurred at a pressure of $<4\times10^{-6}$ torr. $MoO_3$ and Ag had thicknesses of 5.0 nm and 120 nm, respectively. Samples were then encapsulated with glass using an epoxy binder and treated with UV light for 3 min.

Polymer Synthesis

The polymerization can be any conventionally known method of combining the co-monomers, constitutional units or monomers bonded chain or network. In one non-limiting example polymerization can be via Stille cross coupling, Suzuki cross coupling or direct arylation polymerization. In another non-limiting example, the polymers created can be from 2 to 1,000,000 or even greater repeating units.

In one non-limiting example a polymer can be formed by combining 4,7-bis(5-bromo-4-alkylthiophen-2-yl)-5-chloro-6-fluorobenzo[c][1,2,5]thiadiazole, [4-alkyl-5-[5-(trimethylstannyl)thiophen-2-yl]thiophen-2-yl]trimethylstannane, (3,3'-difluoro-[2,2'-bithiophene]-5,5'-diyl)bis(trimethylstannane), $Pd_2dba_3$ and $P(o-tol)_3$ to form the polymer:

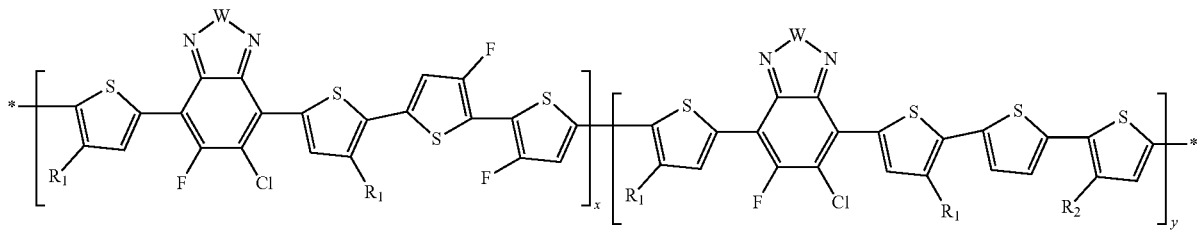

wherein the ratio of x is between 0.6 to 0.8 and y is between 0.2 and 0.4.

In another non-limiting example a polymer can be formed by combining 4,7-bis(5-bromo-4-alkylthiophen-2-yl)-5-chloro-6-fluorobenzo[c][1,2,5]thiadiazole, [4-alkyl-5-[5-(trimethylstannyl)thiophen-2-yl]thiophen-2-yl]trimethylstannane, (3,3'-difluoro-[2,2'-bithiophene]-5,5'-diyl)bis (trimethylstannane), $Pd_2dba_3$ and $P(o-tol)_3$ to form a mixture; degassing the mixture to form a degassed mixture; heating the degassed mixture to form a heated mixture; and cooling the heated mixture to form the polymer:

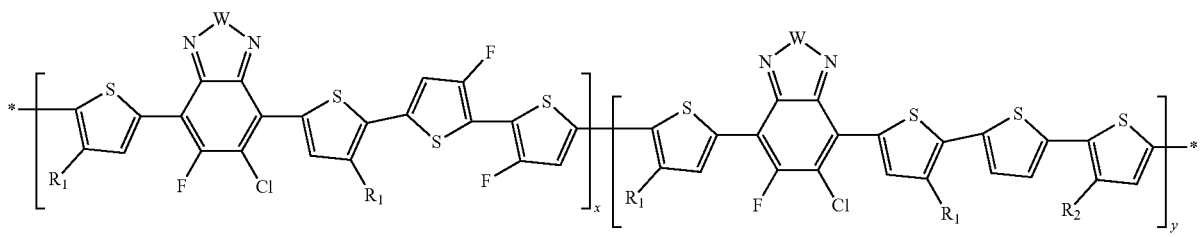

wherein the ratio of x is between 0.6 to 0.8 and y is between 0.2 and 0.4.

In another example, a polymer can be formed by combining 4,7-bis(5-bromo-4-alkyl-thiophen-2-yl)-5-chloro-6-fluorobenzo[c][1,2,5]thiadiazole, (3,3'-difluoro-[2,2'-bithiophene]-5,5'-diyl)bis(trimethylstannane), and benzo[1,2-b:4,5-b']dithiophene-2,6-diyl)bis(trimethylstannane), Pd2dba3 and P(-tol)3 to form the polymer:

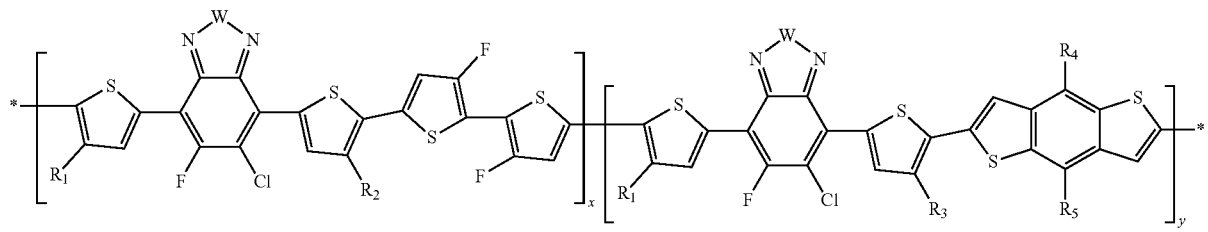

wherein the ratio of x is between 0.6 to 0.8 and y is between 0.2 and 0.4.

In another example, a polymer can be formed by combining 4,7-bis(5-bromo-4-alkyl)thiophen-2-yl)-5-chloro-6-fluorobenzo[c][1,2,5]thiadiazole, (3,3'-difluoro-[2,2'-bithiophene]-5,5'-diyl)bis(trimethylstannane), benzo[1,2-b:4,5-b']dithiophene-2,6-diyl)bis(trimethylstannane)Pd2dba3 and P(o-tol)3 to form a mixture; degassing the mixture to form a degassed mixture; heating the degassed mixture to form a heated mixture; and cooling the heated mixture to form the polymer:

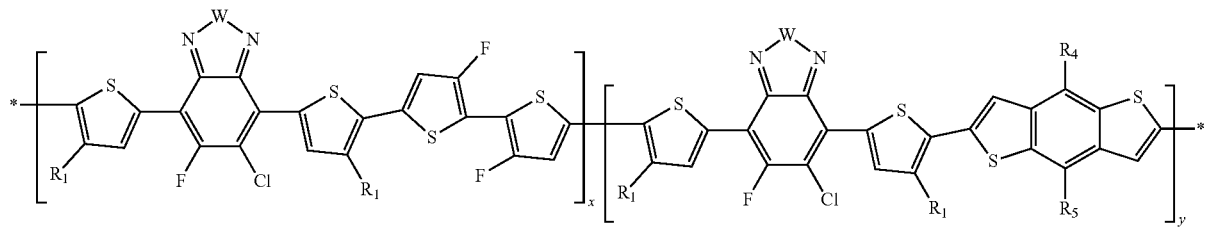

wherein the ratio of x is between 0.6 to 0.8 and y is between 0.2 and 0.4.

Examples of polymerization reactions and polymers.

Non-limiting examples of polymers and the associated polymerization reactions needed to produce them as shown below.

In one embodiment, the polymer can comprise

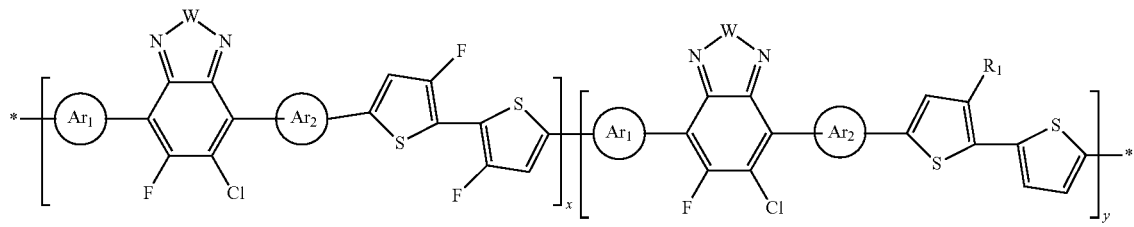

wherein $Ar_1$ and $Ar_2$ are the same or different and independently selected from H or any aryl units. In this polymer, W is selected from the group consisting of: S, Se, O, and N-Q; and Q is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring. Additionally, in the polymer, $R_1$ is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring and wherein x+y=1.

In yet another embodiment, the polymer can be

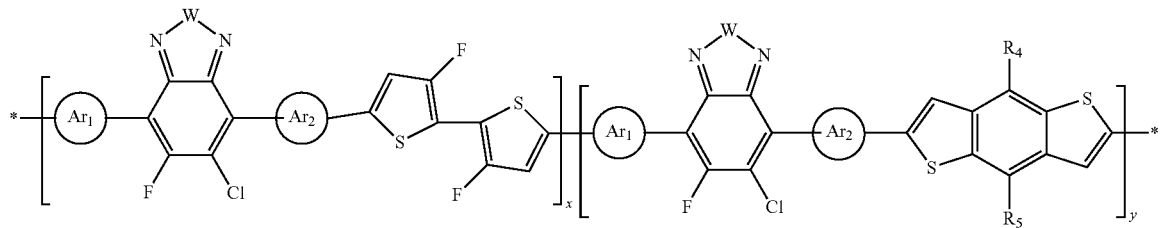

wherein x+y=1,

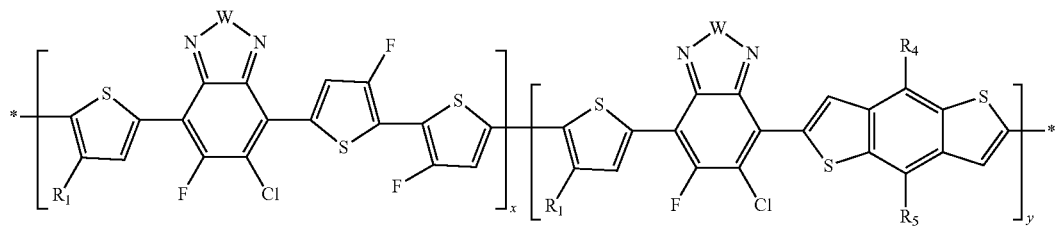

wherein x is from 0.6 to 0.8 and y is from 0.2 to 0.4,

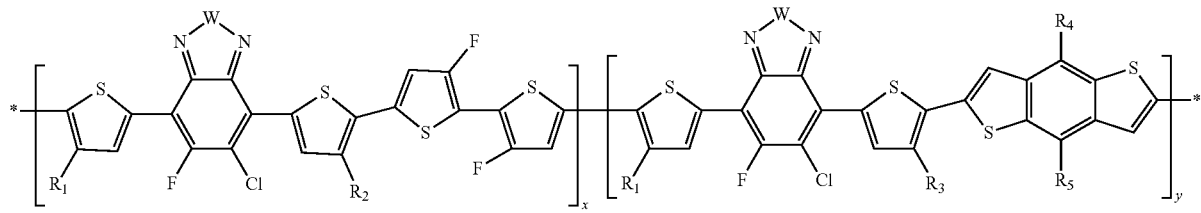

wherein x is from 0.6 to 0.8 and y is from 0.2 to 0.4, or even

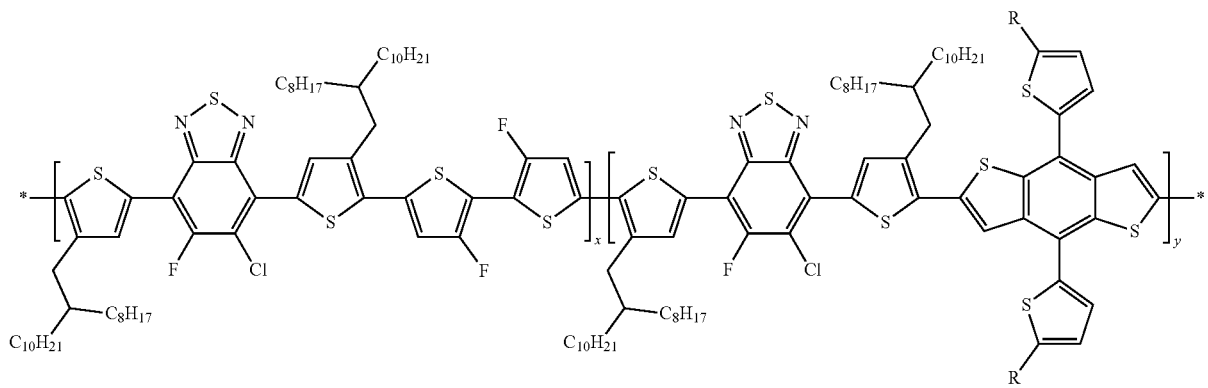

wherein x is from 0.6 to 0.8 and y is from 0.2 to 0.4.

In these embodiments, W can be selected from the group consisting of: S, Se, O, and N-Q; and Q is selected from the group consisting of: a straight-chain or branched carbyl, silyl, or hydrocarbyl, a branched or cyclic alkyl with 1 to 30 atoms, a fused substituted aromatic ring, and a fused unsubstituted aromatic ring. Additionally, $R_1$, $R_4$, and $R_5$ are independently selected from the group consisting of: F, Cl, CN, —OX, —SX, —NH$_2$, —C(=O)X, —C(=O)—OX, —OX, —NHX, —NXX', —C(=O)NHX, —C(=O)NXX', —NO$_2$, CF$_3$, —SF$_5$: a straight-chain or branched carbyl, silyl, or hydrocarbyl, a branched or cyclic alkyl with 1 to 30 atoms, a fused substituted aromatic ring, and a fused unsubstituted aromatic ring. Finally, the fused substituted aromatic ring is fused with a substitution selected from the group consisting of: H, Cl, F, CN, a straight-chain or branched carbyl, silyl, or hydrocarbyl, a branched or cyclic alkyl with 1 to 30 atoms, and an aromatic ring.

Additionally,

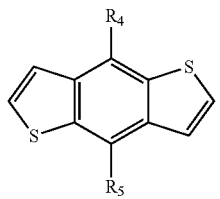

can be selected from the group consisting of:

In this embodiment, W could be S, Se, O, or N-Q; Q can be a straight-chain carbyl, silyl or hydrocarbyl, branched, cyclic alkyl with 1 to 30 atoms, fused aromatic rings, which can be optionally substituted with one or more X or X' groups. $R_1$ can be selected from F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups. $R_2$ and $R_3$ can be the same of different and independently selected from any halogen such as fluorine, chlorine. In this embodiment, wherein the ratio of h, j, i, and k are h+j is between 0.2 to 0.6, or more narrowly 0.4, and i+k is between 0.4 and 0.8 or more narrowly 0.6.

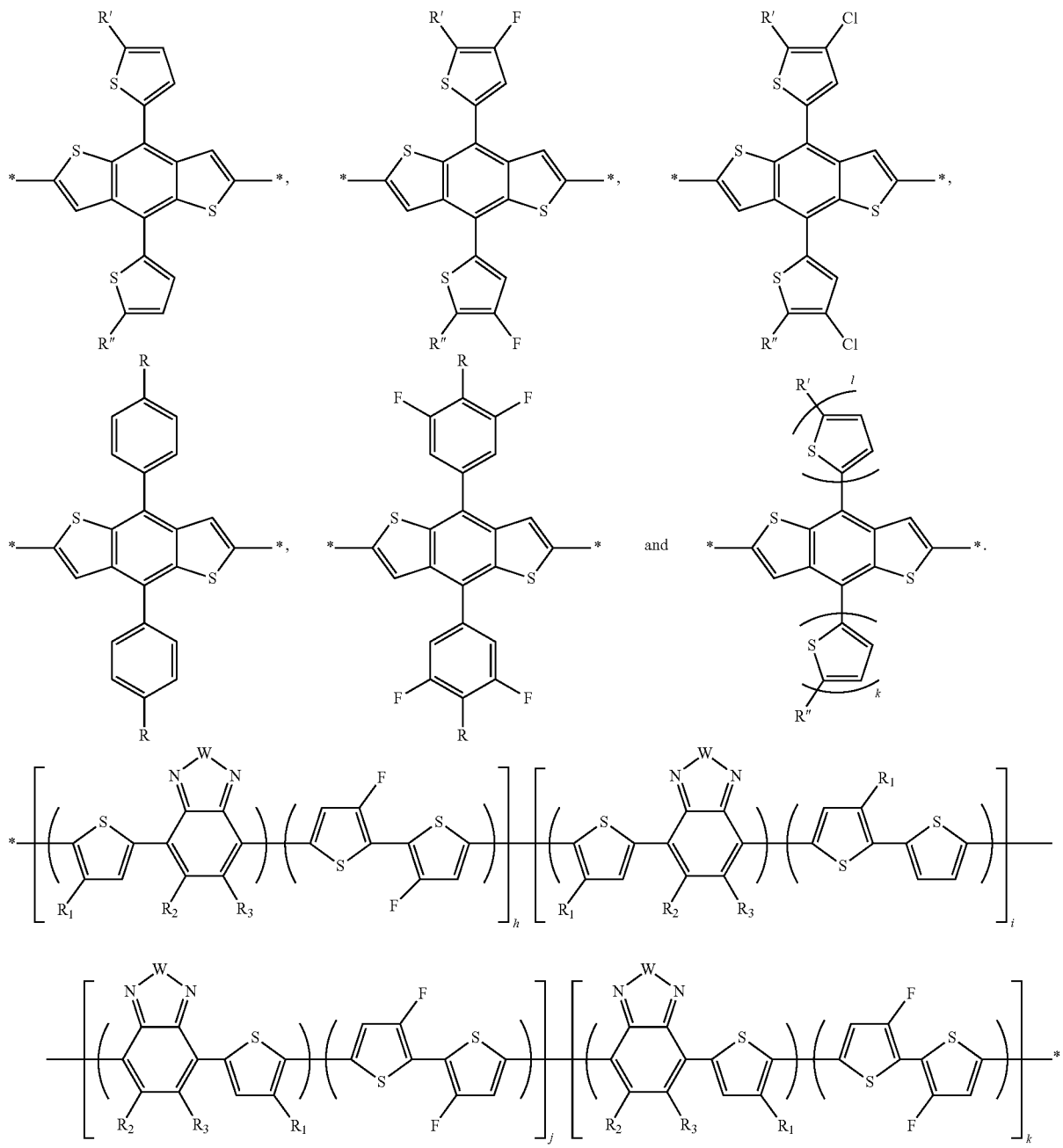

In a more narrowing embodiment, polymer A can be

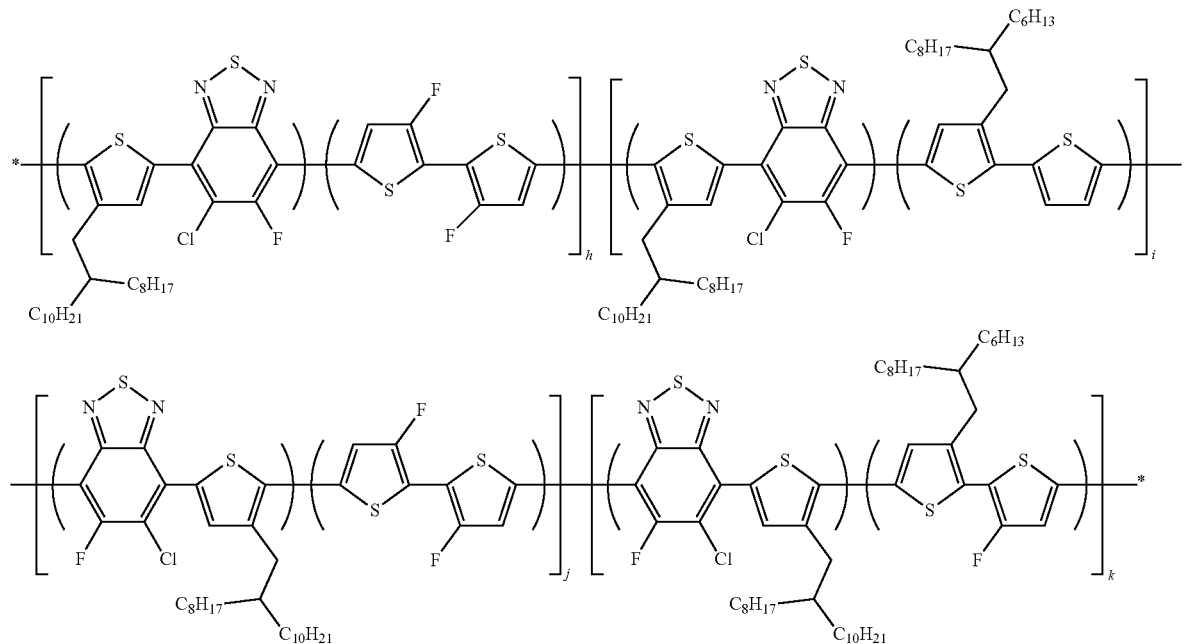

Figure 18:
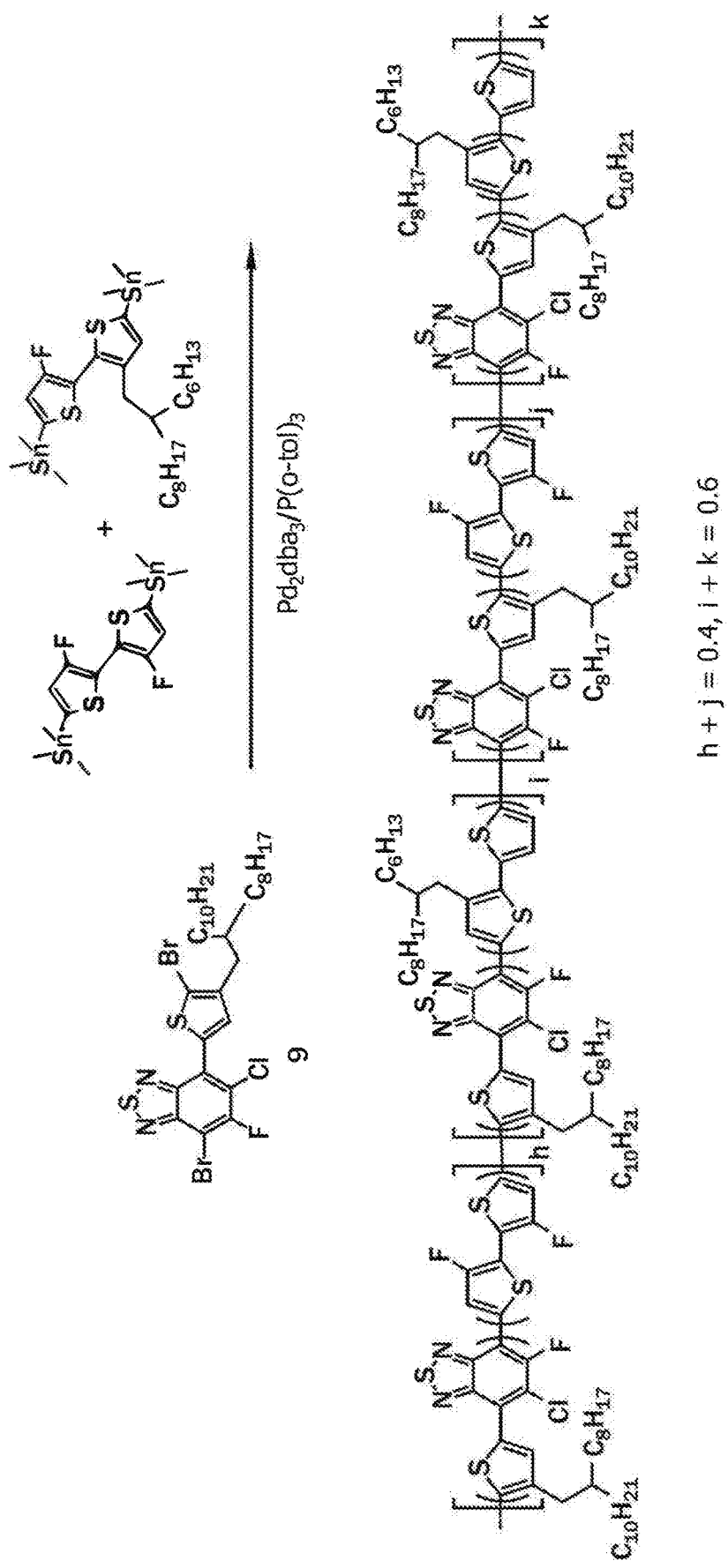
FIG. 18 depicts a reaction mechanism.

In a non-limiting method of manufacturing Polymer A, 4-bromo-7-[5-bromo-4-(alkyl)thiophen-2-yl]-6-chloro-5-fluoro-2,1,3-benzothiadiazole, (3,3'-difluoro-[2,2'-bithiophene]-5,5'-diyl)bis(trimethylstannane), [4-(2-hexyldecyl)-5-[5-(trimethylstannyl)thiophen-2-yl]thiophen-2-yl]trimethylstannane, Pd2dba3 tris(dibenzylideneacetone); and dipalladium P(o-tol)3 tris(2-methylphenyl)phosphane were combined. The mixture was degassed with argon and anhydrous o-dichlorobenzene was injected. The solution was heated then cooled to room temperature. The product was precipitated by pouring the solution into methanol. The solid was purified by Soxhlet extraction. The chloroform portion contained the main product after reprecipitation by methanol and then dried overnight. The viscosity of the polymer in pure chlorobenzene with the concentration of 10 mg/mL is 1.07 mPa·s at 25° C. FIG. 18 depicts one non-limiting method of manufacturing Polymer A.

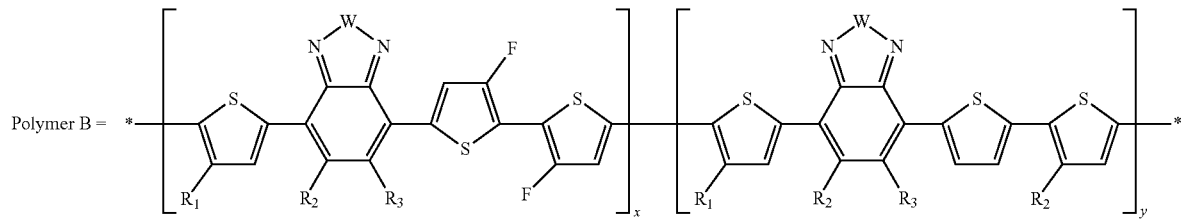

In this embodiment, W could be S, Se, O, or N-Q; Q can be a straight-chain carbyl, silyl or hydrocarbyl, branched, cyclic alkyl with 1 to 30 atoms, fused aromatic rings, which can be optionally substituted with one or more X or X' groups. $R_1$ can be selected from F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, —CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups. $R_2$ and $R_3$ can be the same of different and independently selected from any halogen such as fluorine, chlorine. In this embodiment, wherein the ratio of x is between 0.6 to 0.8, or more narrowly 0.6, and y is between 0.2 and 0.4 or more narrowly 0.3.

In a more narrowing embodiment, polymer B can be:

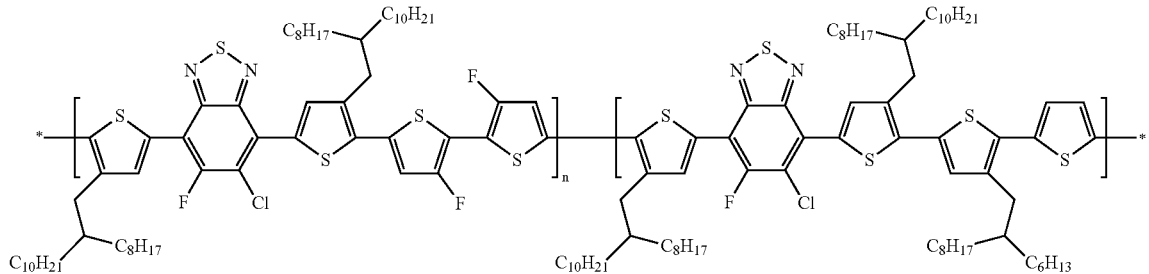

In a non-limiting method of manufacturing Polymer B, 4,7-bis(5-bromo-4-(alkyl)thiophen-2-yl)-5-chloro-6-fluorobenzo[c][1,2,5]thiadiazole, compound [4-(2-hexyldecyl)-5-[5-(trimethylstannyl)thiophen-2-yl]thiophen-2-yl]trimethylstannane, compound [4-(2-hexyldecyl)-5-[5-(trimethylstannyl)thiophen-2-yl]thiophen-2-yl] trimethylstannane, Pd2dba3 and P(o-tol)3 were added. The mixture was degassed with argon before anhydrous chlorobenzene was added. The solution was heated then cooled to room temperature. The solid was filtered and purified by Soxhlet extraction with acetone, hexane, dichloromethane and chloroform. The chloroform portion contained the main product and was reprecipitated by methanol and dried overnight. The viscosity of the polymer in chlorobenzene/dichlorobenzene (v/v, 1:1) with the concentration of 10 mg/mL is 1.64 mPa·s at 25° C.

Polymer C = 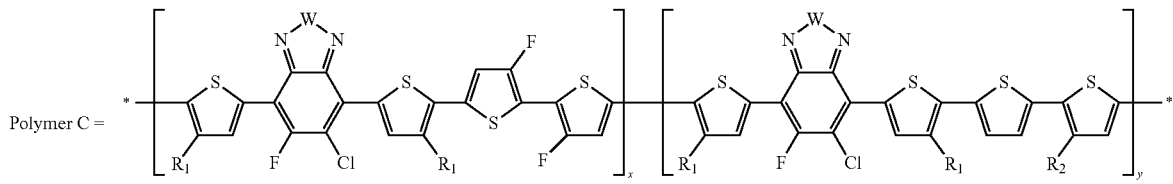

In this embodiment, W could be S, Se, O, or N-Q; Q can be a straight-chain carbyl, silyl or hydrocarbyl, branched, cyclic alkyl with 1 to 30 atoms, fused aromatic rings, which can be optionally substituted with one or more X or X' groups. $R_1$ can be selected from F, Cl, I, Br, CN, —NCO, —NCS, —OCN, —SCN, —OX, —SX, —NH$_2$, —C(=O)X, —C(=O)—OX, —OX, —NHX, —NXX', —C(=O)NHX, —C(=O)NXX', —SO$_3$X, —SO$_2$X, —OH, —NO$_2$, CF$_3$, —SF$_5$, or straight-chain carbyl, silyl or hydrocarbyl, branched, cyclic alkyl with 1 to 30 atoms, fused aromatic rings, which can be optionally substituted with one or more X or X' groups. $R_2$ and $R_3$ can be the same of different and independently selected from any halogen such as fluorine, chlorine, bromine and iodine. $R_4$ and $R_5$ can be the same or different and independently selected from straight-chain carbyl, silyl or hydrocarbyl, branched, cyclic alkyl with 1 to 30 atoms, fused aromatic rings, which can be optionally substituted with one or more X or X' groups. In this embodiment, wherein the ratio of x is between 0.6 to 0.8, or more narrowly 0.6, and y is between 0.2 and 0.4 or more narrowly 0.3.

In a more narrowing embodiment, polymer C can be:

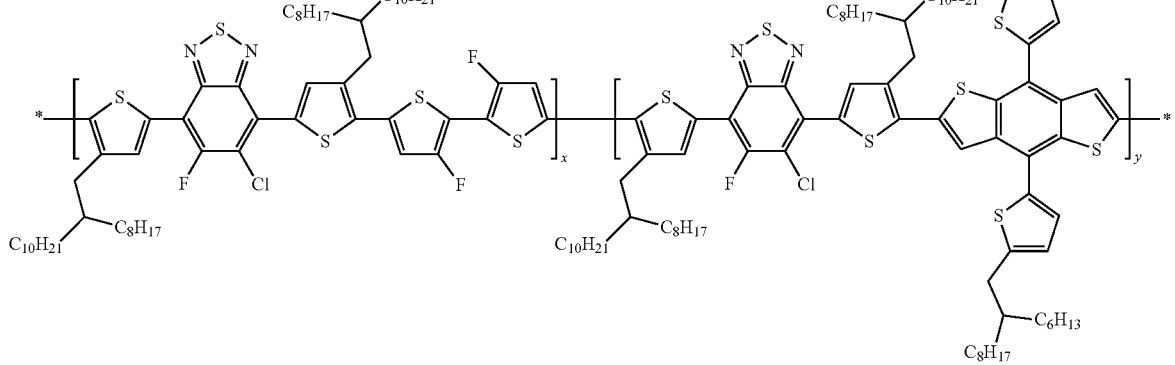

In other narrowing embodiments, polymer C can be:

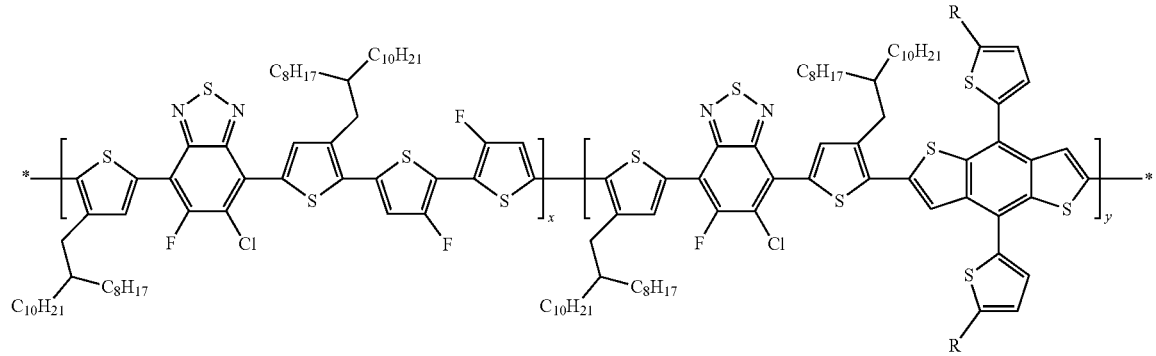

In this embodiment, R can be any combination of 2-hexyldecyl, 2-butyloctyl, or 2-ethyldexyl. In these embodiments, x and y can be 0.7:0.3 respectfully, 0.5:0.5, or x is from 0.6 to 0.8 and y is from 0.2 to 0.4. The device performance of the different R's and x:y ratios are shown below in Table 1.

TABLE 1

| R & x:y ratios | Voc (V) | Jsc (mA/cm2) | FF (%) | PCE (%) |
|---|---|---|---|---|
| 2-butyloctyl x = 0.7 y = 0.3 | 0.817 | 17.7 | 71.2 | 10.3 |
| 2-ethylhexyl x = 0.7 y = 0.3 | 0.811 | 17.3 | 74.9 | 10.7 |
| 2-ethylhexyl x = 0.5 y = 0.5 | 0.799 | 18.6 | 64.5 | 9.59 |

Jsc (mA/cm$^2$) Short-circuit current density (Jsc) is the current density that flows out of the solar cell at zero bias. $V_{oc}$ (V) Open-circuit voltage ($V_{oc}$) is the voltage for which the current in the external circuit is zero. Fill factor percentage (FF %) is the ratio of the maximum power point divided by the open circuit voltage and the short circuit current. PCE (%) The power conversion efficiency (PCE) of a photovoltaic cell is the percentage of the solar energy shining on a photovoltaic device that is converted into usable electricity.

Figure 19:
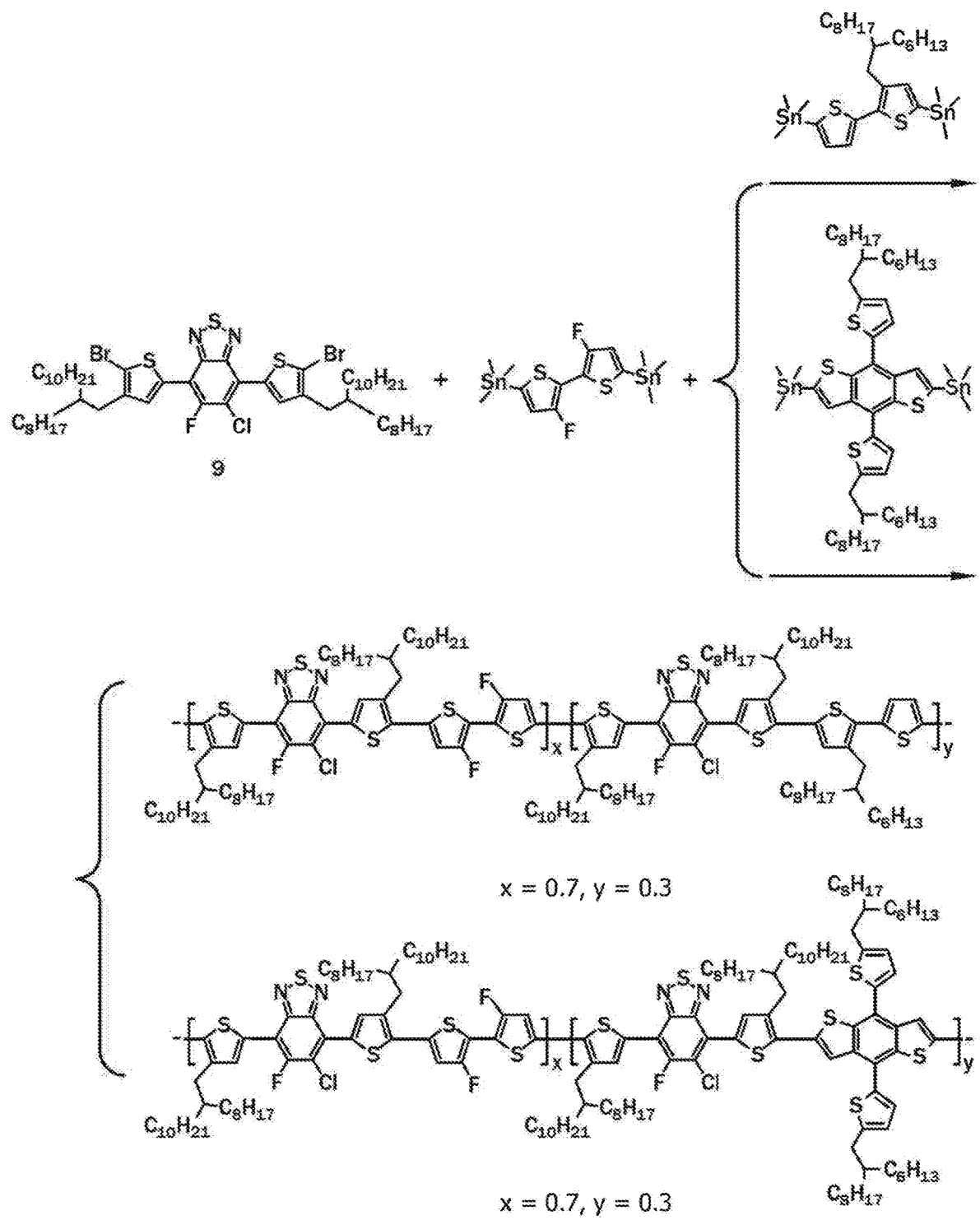
FIG. 19 depicts a reaction mechanism.

In a non-limiting method of manufacturing Polymer C, 4,7-bis(5-bromo-4-(alkyl)thiophen-2-yl)-5-chloro-6-fluorobenzo[c][1,2,5]thiadiazole, compound [4-(2-hexyldecyl)-5-[5-(trimethylstannyl)thiophen-2-yl]thiophen-2-yl]trimethylstannane, compound [4-(2-hexyldecyl)-5-[5-(trimethylstannyl)thiophen-2-yl]thiophen-2-yl] trimethylstannane, Pd2dba3 and P(o-tol)3 were added. The mixture was degassed with argon before anhydrous chlorobenzene was added. The solution was heated then cooled to room temperature. The solid was filtered and purified by Soxhlet extraction with acetone, hexane, dichloromethane and chloroform. The chloroform portion contained the main product and was reprecipitated by methanol and dried overnight. The viscosity of the polymer in chlorobenzene/dichlorobenzene (v/v, 1:1) with the concentration of 10 mg/mL is 1.50 mPa·s at 25° C. FIG. 19 depicts a non-limiting method of manufacturing Polymer B and Polymer C.

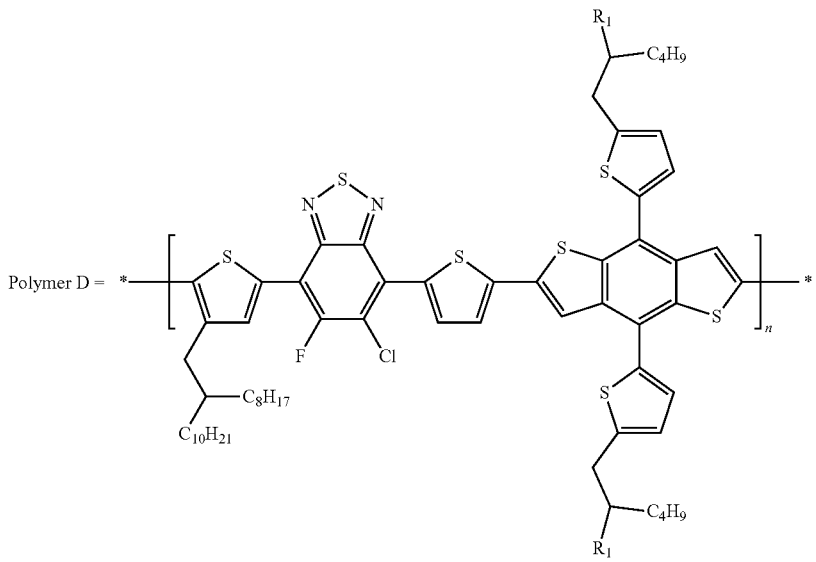

wherein $R_1$ is $C_6H_{13}$.

In a non-limiting embodiment, polymer D can be formed by combining 4-(5-bromo-4-(alkyl)thiophen-2-yl)-7-(5-bromothiophen-2-yl)-6-chloro-5-fluorobenzo[c][1,2,5]thiadiazole, (4,8-bis(5-(2-butyloctyl)thiophen-2-yl)benzo[1,2-b:4,5-b']dithiophene-2,6-diyl)bis(trimethylstannane), Pd2dba3 and P(o-tol)3 together. The mixture is then degassed with argon before adding anhydrous chlorobenzene. The solution is then heated followed by chloroform addition. The solid was filtered and purified by Soxhlet extraction with methanol, hexane and chloroform. The viscosity in chlorobenzene/dichlorobenzene (v/v, 1:1) with concentration of 10 mg/mL is 1.255 mPa·s at 25° C.

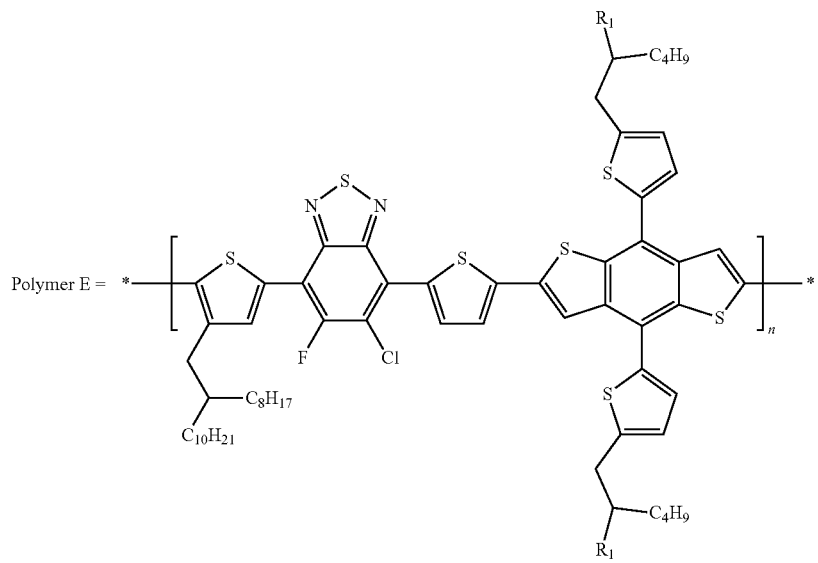

wherein $R_1$ is $C_2H_5$.

In a non-limiting embodiment, polymer E can be formed by combining 4-(5-bromo-4-(alkyl)thiophen-2-yl)-7-(5-bromothiophen-2-yl)-6-chloro-5-fluorobenzo[c][1,2,5]thiadiazole, compound (4,8-bis(5-(2-ethylhexyl)thiophen-2-yl)benzo[1,2-b:4,5-b']dithiophene-2,6-diyl)bis(trimethylstannane), Pd2dba3 and P(o-tol)3. The mixture is then degassed before adding anhydrous dichlorobenzene. The solution was heated and poured into methanol. The solid was filtered and purified by Soxhlet extraction with acetone, hexane and dichloromethane. The solid product was collected from the dichloromethane portion, reprecipitated with methanol, and dried overnight. The viscosity in chlorobenzene/dichlorobenzene (v/v, 1:1) with concentration of 10 mg/mL is 1.15 mPa·s at 25° C.

In a 25-mL Schlenk flask, 4,7-bis(5-bromo-4-(alkyl)thiophen-2-yl)-5-chloro-6-fluorobenzo[c][1,2,5]thiadiazole (100.0 mg, 0.093 mmol), 5,5'-bis(trimethylstannyl)-2,2'-bithiophene (46.7 mg, 0.095 mmol), $Pd_2dba_3$ (1.1 mg, 0.001 mmol) and $P(o-tol)_3$ (2.4 mg, 0.008 mmol) were added. The mixture was degassed with argon three times before 1.6 mL of anhydrous chlorobenzene was added. The mixture was further degassed with two freeze-vacuum-thaw cycles. The solution was heated at 90° C. for 10 mins and at 120° C. for 48 hours to avoid overheating. The mixture was poured into methanol after cooling to room temperature. The solid was filtered and purified by Soxhlet extraction with acetone (16 hours), hexane (3 hours) chloroform (4 hours) and chlorobenzene (5 hours). The recovered polymer consisted of 27 mg (yield, 26.3%) from the chloroform portion, 8 mg (yield, 7.8%) from the chlorobenzene portion and 65 mg remained insoluble in the thimble.

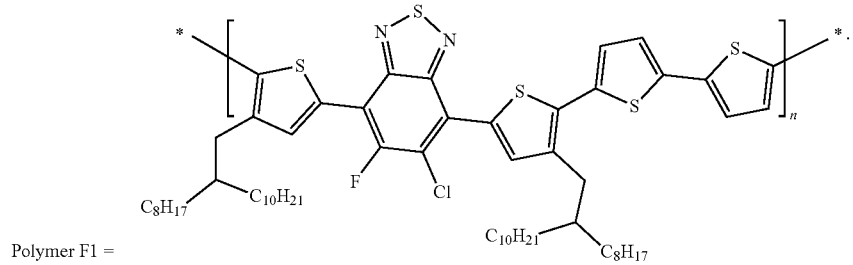

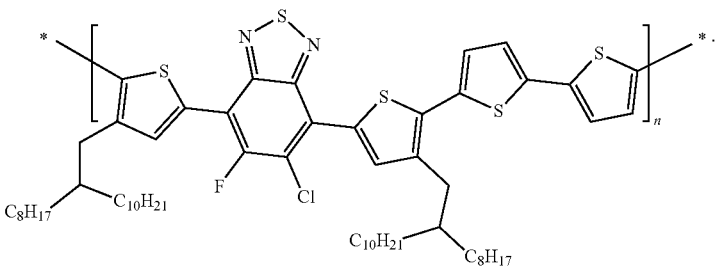

Polymer F2 =

In a 25-mL Schlenk flask, 4,7-bis(5-bromo-4-(alkyl)thiophen-2-yl)-5-chloro-6-fluorobenzo[c][1,2,5]thiadiazole (100.0 mg, 0.093 mmol), 5,5'-bis(trimethylstannyl)-2,2'-bithiophene (46.7 mg, 0.095 mmol) and P(o-tol)$_3$ (2.4 mg, 0.008 mmol) were added. The flask was degassed with argon three times before 1.6 mL of anhydrous dichlorobenzene was added. The solution was heated at 135° C. for 48 hours. The mixture was poured into methanol after cooling to room temperature. The solid was filtered and purified by Soxhlet extraction with acetone (8 hours), hexane (16 hours) and chloroform (3 hours). There was nothing left in the thimble. The chloroform portion was the main product (88 mg, yield, 85.6%). It was collected after reprecipitation from methanol and dried overnight. The viscosity of the polymer in chlorobenzene/dichlorobenzene (v/v, 1:1) with the concentration of 10 mg/mL is 1.36 mPa·s at 25°.

In the above polymerizations, dichlorobenzene was used in most of the reactions since when using chlorobenzene as the solvent, the yield significantly decreased from 85.6% to 34.1% due to crosslinking in the polymer as shown in Table 2 below.

flask, (5-(2-ethylhexyl)thiophen-2-yl)trimethylstannane (260 mg, 0.724 mmol), 4-bromo-6-chloro-5-fluoro-7-(thiophen-2-yl)benzo[c][1,2,5]thiadiazole (230 mg, 0.658 mmol), Pd$_2$dba$_3$ (12 mg, 0.013 mmol) and P(o-tol)$_3$ (16 mg, 0.053 mmol) were combined. The mixture was degassed three times before 7.7 mL of anhydrous toluene was injected. The solution was heated to 105° C. for 48 h and then cooled to room temperature. The toluene solvent was removed by a rotary evaporator, and the resulting residue was purified by using silica gel column chromatography with hexane/dichloromethane mixture as the eluent. The two products were collected as separate fractions. The compounds were both recrystallized from the solvent mixture of iso-propanol/methanol to yield compound 5-chloro-7-(5-(2-ethylhexyl)thiophen-2-yl)-6-fluoro-4-(thiophen-2-yl)benzo[c][1,2,5]thiadiazole (0.13 g, yield 31.6%) and 4,6-bis(5-(2-ethylhexyl)thiophen-2-yl)-5-fluoro-7-(thiophen-2-yl)benzo[c][1,2,5]thiadiazole (0.04 g, yield 13.1%) as orange crystals.

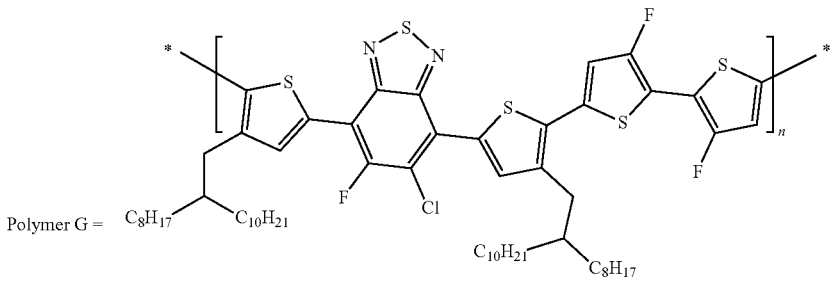

Polymer G =

TABLE 2

| Polymers | Solvent | Yield (%) |
| --- | --- | --- |
| Polymer F-1 | Chlorobenzene | 34.1 |
| Polymer F-2 | Dichlorobenzene | 85.6 |

Figure 20:
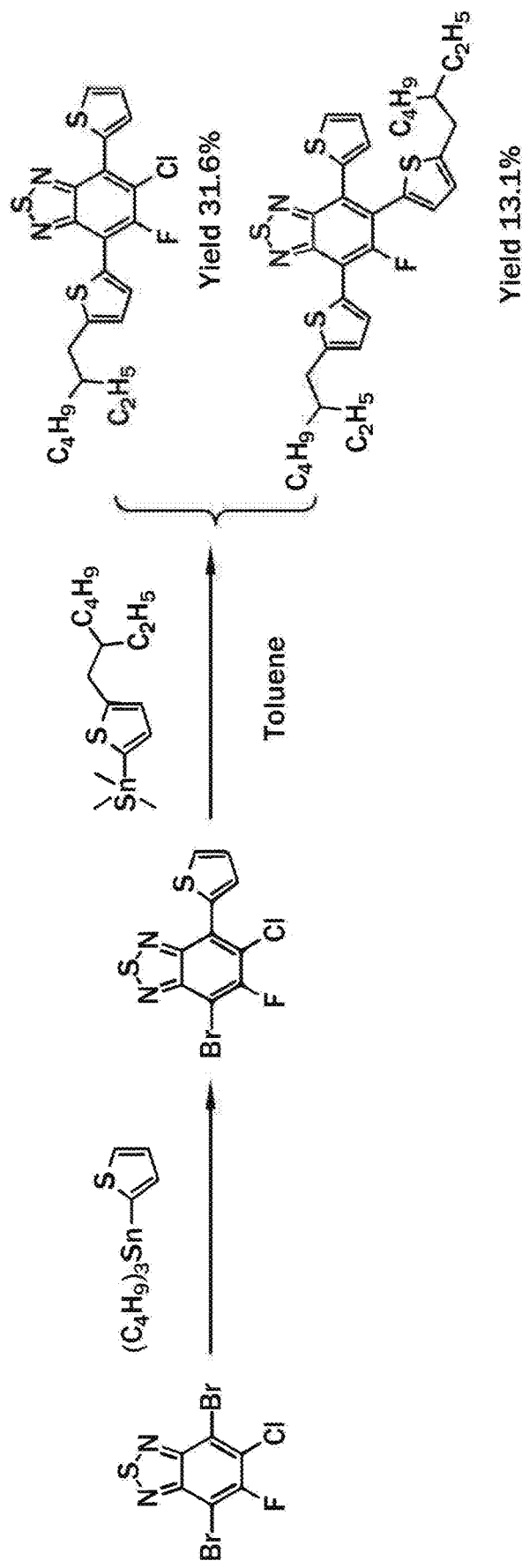
FIG. 20 depicts a reaction mechanism.

It is theorized that using a solvent that selected from the group consisting of: dichlorobenzene, trichlorobenzene, or combinations thereof would allow of selectivity yields greater than 40%, 50%, 60%, 70%, even 80%. As shown in FIG. 20, the reaction mechanism for F1 and F2 provided low yields when performed without the appropriate solvent. It is theorized that the chlorine atom participates in the coupling reaction with tin compound leading to crosslinking.

Synthesis of 5-chloro-7-(5-(2-ethylhexyl)thiophen-2-yl)-6-fluoro-4-(thiophen-2-yl)benzo[c][1,2,5]thiadiazole 4 and 4,6-bis(5-(2-ethylhexyl)thiophen-2-yl)-5-fluoro-7-(thiophen-2-yl)benzo[c][1,2,5]thiadiazole 5: In a 25 mL Schlenk In a non-limiting embodiment, Polymer G can be formed by combining 4,7-bis(5-bromo-4-(alkyl)thiophen-2-yl)-5-chloro-6-fluorobenzo[c][1,2,5]thiadiazole, compound (3,3'-difluoro-[2,2'-bithiophene]-5,5'-diyl)bis(trimethylstannane), Pd2dba3 and P(o-tol)3 were added. The solution was degassed before anhydrous dichlorobenzene was added. The solution was then heated and cooled to room temperature. The solid was filtered and purified by Soxhlet extraction with acetone, hexane, dichloromethane, chloroform and chlorobenzene.

Electron Transport Layer:

Zinc tin oxide (ZTO): phenyl-C$_{60}$-butyric acid-2-N,N,N-trimethylammonium iodide ethyl ester (PCBNMI) sol-gel solutions were prepared by adding zinc acetate dihydrate (996 mg), tin (II) acetate (99.6 mg), and PCBNOH (5 mg) to 2-methoxyethanol (10 mL) and ethanolamine (249 μL). Solutions were stirred for a minimum of 8 hours before use.

An Erichsen COATMASTER 510 was used to spread the electron transport layer on the large area ITO substrates.

Approximately 300 μL of the zinc tin oxide:fullerene (ZTO: PCBNMI) sol-gel solution was drawn into a pipette and deposited without filtration, directly onto the ITO at room temperature.

Table 3 below depicts the average device performance of the above-mentioned polymers.

TABLE 3

| Active Layer | Voc (V) | Jsc (mA/cm2) | FF (%) | PCE (%) |
|---|---|---|---|---|
| Polymer A | 0.79 | 17.44 | 65.8 | 8.73 |
| Polymer B | 0.829 | 15.5 | 74.3 | 9.5 |
| Polymer C | 0.853 | 16.8 | 69.6 | 9.98 |
| Polymer D | 0.872 | 9.42 | 66.3 | 5.44 |
| Polymer E | 0.823 | 15.24 | 65.1 | 8.16 |
| Polymer F | 0.731 | 16.2 | 71.4 | 8.46 |
| Polymer G | 0.815 | 12.8 | 45.5 | 4.76 |

Jsc (mA/cm$^2$) Short-circuit current density (Jsc) is the current density that flows out of the solar cell at zero bias. $V_{oc}$ (V) Open-circuit voltage ($V_{oc}$) is the voltage for which the current in the external circuit is zero. Fill factor percentage (FF %) is the ratio of the maximum power point divided by the open circuit voltage and the short circuit current. PCE (%) The power conversion efficiency (PCE) of a photovoltaic cell is the percentage of the solar energy shining on a photovoltaic device that is converted into usable electricity.

Devices in which the photovoltaic polymer, copolymer, unit, or process can be used in include, but are not limited to general organic photovoltaic devices, organic light emitting diodes, transistors, photodetectors, and radio frequency identification tags.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A comonomer comprising:

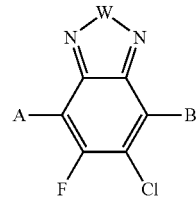

wherein W is S, and wherein A and B are independently selected from the group consisting of: an aryl group, and a heteroaryl group and
wherein the heteroaryl group is connected to a Br and the heteroaryl is not a 5-bromo-2-thienyl.

2. The comonomer of claim 1, wherein A and B are identical.

3. A comonomer comprising:

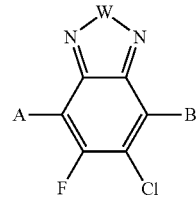

wherein W is and wherein A and B are independently selected from the group consisting of an aryl group, and a heteroaryl group and wherein the aryl group is connected to a Br,
and wherein the heteroaryl group is connected to a Br and the heteroaryl is not a 5-bromo-2-thienyl.

4. A comonomer comprising:

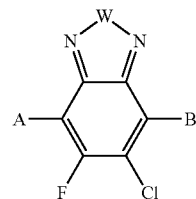

wherein W is selected from S, and
A and B are independently selected from the group consisting of: an aryl group, an aryl group connected to a Br, a heteroaryl group, and a heteroaryl group is connected to a Br and the heteroaryl is not a 5-bromo-2-thienyl.

5. The comonomer of claim 4, wherein A and B are identical.

* * * * *